US012734235B2

(12) United States Patent
Prokofyev et al.

(10) Patent No.: US 12,734,235 B2
(45) Date of Patent: Sep. 15, 2026

(54) AAV5-BASED VACCINE AGAINST SARS-CoV-2

(71) Applicant: JOINT STOCK COMPANY "BIOCAD", Saint Petersburg (RU)

(72) Inventors: Alexander Vladimirovich Prokofyev, Saint Petersburg (RU); Pavel Mikhailovich Gershovich, Saint Petersburg (RU); Anna Nikolaevna Strelkova, g. Yaransk (RU); Natalia Aleksandrovna Spirina, Saint Petersburg (RU); Diana Aleksandrovna Kondinskaia, Saint Petersburg (RU); Pavel Andreevich Iakovlev, Saint Petersburg (RU); Dmitry Valentinovich Morozov, Saint Petersburg (RU)

( * ) Notice: Subject to any disclaimer, the term of this patent is extended or adjusted under 35 U.S.C. 154(b) by 721 days.

(21) Appl. No.: 18/043,354

(22) PCT Filed: Aug. 27, 2021

(86) PCT No.: PCT/RU2021/050279
§ 371 (c)(1),
(2) Date: Feb. 28, 2023

(87) PCT Pub. No.: WO2022/045935
PCT Pub. Date: Mar. 3, 2022

(65) Prior Publication Data
US 2023/0321220 A1 Oct. 12, 2023

(30) Foreign Application Priority Data
Aug. 28, 2020 (RU) ........................... RU2020128658

(51) Int. Cl.

| | |
|---|---|
| ***A61K 39/215*** | (2006.01) |
| ***A61P 31/12*** | (2006.01) |
| ***C07K 14/005*** | (2006.01) |
| ***C07K 14/61*** | (2006.01) |
| ***C12N 15/86*** | (2006.01) |
| ***C12N 15/861*** | (2006.01) |
| *A61K 39/00* | (2006.01) |

(52) U.S. Cl.
CPC ............ *A61K 39/215* (2013.01); *A61P 31/12* (2018.01); *C07K 14/005* (2013.01); *C07K 14/61* (2013.01); *C12N 15/86* (2013.01); *A61K 2039/5256* (2013.01); *C07K 2319/02* (2013.01); *C12N 15/861* (2013.01); *C12N 2750/14143* (2013.01); *C12N 2770/20022* (2013.01); *C12N 2770/20034* (2013.01); *C12N 2770/20071* (2013.01)

(58) Field of Classification Search
None
See application file for complete search history.

(56) References Cited

U.S. PATENT DOCUMENTS

| | | | |
|---|---|---|---|
| 4,399,216 | A | 8/1983 | Axel et al. |
| 4,634,665 | A | 1/1987 | Axel et al. |
| 5,179,017 | A | 1/1993 | Axel et al. |

FOREIGN PATENT DOCUMENTS

| | | | |
|---|---|---|---|
| CN | 110951756 | B | 8/2020 |
| CN | 110974950 | B | 8/2020 |
| CN | 111518175 | A | 8/2020 |
| CN | 111533809 | A | 8/2020 |
| CN | 111560354 | A | 8/2020 |
| RU | 2720614 | C1 | 5/2020 |
| RU | 2723008 | C1 | 6/2020 |
| RU | 2733831 | C1 | 10/2020 |
| RU | 2733832 | C1 | 10/2020 |
| RU | 2733834 | C1 | 10/2020 |

OTHER PUBLICATIONS

Corresponding Russian application No. 2020128658 search report dated Jan. 11, 2021 (Machine translation provided).
Corresponding Russian application No. 2020128658 Office Action dated Jan. 18, 2021 (Machine translation provided).
Corresponding Russian application No. 2020128658 Office Action dated Apr. 28, 2021 (Machine translation provided).
Corresponding Russian application No. 2020128658 Grant decision dated Sep. 5, 2022 (Machine translation provided).
International application No. PCT/RU2021/050279 International Search Report dated Nov. 18, 2021.
International application No. PCT/RU2021/050279 Written Opinion of the International Searching Authority dated Nov. 18, 2021.
The GenBank database, Wu F., Severe acute respiratory syndrome coronavirus 2 isolate Wuhan-Hu-1, complete genome, 2020, GenBank: MN908947.3 (https://www.ncbi.nlm.nih.gov/nuccore/MN908947).
Fan Wu et al., A new coronavirus associated with human respiratory disease in China, 2020, Nature, vol. 579, pp. 265-269 (https://www.nature.com/articles/s41586-020-2008-3.
Mori, S. et al., 2004, Two novel adeno-associated viruses from cynomolgus monkey: pseudotyping characterization of capsid protein. Virology. vol. 330, Issue 2, Dec. 20, 2004, pp. 375-383.

(Continued)

*Primary Examiner* — Nicole Kinsey White
(74) *Attorney, Agent, or Firm* — Anglehart et al.

(57) ABSTRACT

The present application relates to the fields of biotechnology, immunology, virology, genetics, and molecular biology. More specifically, the present invention relates to an isolated recombinant receptor-binding domain of the S glycoprotein (RBD-S) of SARS-CoV-2 (severe acute respiratory syndrome-related coronavirus 2), to a nucleic acid that encodes RBD-S of SARS-CoV-2, to an expression cassette and a vector based thereon, as well as to a recombinant AAV5 (adeno-associated vims serotype 5)-based virus for the induction of specific immunity to SARS-CoV-2 and/or prevention of the SARS-CoV-2-related coronavirus infection, to an AAV5-based vaccine for the induction of specific immunity to SARS-CoV-2 and/or prevention of the SARS-CoV-2-related coronavirus infection, and to their use for the induction of specific immunity to SARS-CoV-2 and/or prevention of the SARS-CoV-2-related coronavirus infection.

21 Claims, 10 Drawing Sheets

Specification includes a Sequence Listing.

(56) References Cited

OTHER PUBLICATIONS

McLaughlin et al., Adeno-associated virus general transduction vectors: analysis of proviral structures. Journalofvirology,Jun. 1988,p. 1963-1973.

Miao Gui, et al., Cryo-electron microscopy structures of the SARS-CoV spike glycoprotein reveal a prerequisite conformational state for receptor binding, 2017, Cell Res. 27, p. 119-129.

European application No. 21862185.2, the extended European search report dated Jul. 22, 2024.

Nieto Karen et al., AAV Vectors Vaccines Against Infectious Diseases. Frontiers in Immunology, vol. 5, Jan. 21, 2014.

Samrat Subodh Kumar et al., Prospect of SARS-CoV-2 spike protein: Potential role in vaccine and therapeutic development. Virus Research, Amsterdam, NL, vol. 288, Aug. 23, 2020.

Samrat Subodh Kumar et al., Rational design and engineering of therapeutic proteins. Drug Discovery Today, Elsevier, Amsterdam, NL, vol. 8, No. 5, Mar. 1, 2023, pp. 212-221.

AAV5-BASED VACCINE AGAINST SARS-CoV-2

The content of the ASCII text file of the sequence listing named "P2507US00-Sequence-Listing-v6" which is 54 kb in size was created on Jun. 7, 2023 and electronically submitted herewith via EFS-Web is incorporated herein by reference.

FIELD OF INVENTION

The present application relates to the fields of biotechnology, immunology, virology, genetics, and molecular biology. More specifically, the present invention relates to an isolated recombinant receptor-binding domain of the S glycoprotein (RBD-S) of SARS-CoV-2 (severe acute respiratory syndrome-related coronavirus 2), to a nucleic acid that encodes RBD-S of SARS-CoV-2, to an expression cassette and a vector based thereon, as well as to a recombinant AAV5 (adeno-associated virus serotype 5)-based virus for the induction of specific immunity to SARS-CoV-2 and/or prevention of the SARS-CoV-2-related coronavirus infection, to an AAV5-based vaccine for the induction of specific immunity to SARS-CoV-2 and/or prevention of the SARS-CoV-2-related coronavirus infection, and to their use for the induction of specific immunity to SARS-CoV-2 and/or prevention of the SARS-CoV-2-related coronavirus infection.

BACKGROUND OF INVENTION

The SARS-CoV-2 (severe acute respiratory syndrome coronavirus 2) is a member of the Sarbecovirus subgenus of the Betacoronavirus genus.

SARS-CoV-2 was identified in December 2019 as a result of the analysis of samples taken from patients with pneumonia. On Dec. 31, 2019, the World Health Organization was informed of several cases of viral pneumonia caused by a previously unknown pathogen. The complete genome of the virus was first decoded in China.

Coronaviruses, which include SARS-CoV-2, typically cause acute respiratory diseases. This family also includes SARS-CoV and MERS-CoV, which cause severe acute respiratory syndrome and Middle East respiratory syndrome, respectively.

SARS-CoV-2 is responsible for the ongoing COVID-19 pandemic. The World Health Organization in January 2020 declared the SARS-CoV-2 outbreak a public health emergency of international concern, and on Mar. 11, 2020, it characterized the worldwide spread of the disease as a pandemic.

The GenBank database, Wu F., Severe acute respiratory syndrome coronavirus 2 isolate Wuhan-Hu-1, complete genome, 2020, GenBank: MN908947.3 and the article by Fan Wu ET AL., A new coronavirus associated with human respiratory disease in China, 2020, Nature, volume 579, pages 265-269 provide the information on the SARS-CoV-2 genome.

The patent document CN110951756 (B) discloses nucleotide acid sequences encoding a SARS-CoV-2 antigen peptide and provides that these nucleotide acid sequences may be used to induce appropriate immune responses; it is expected that they will be used in vaccines against SARS-CoV-2.

The patent document CN110974950B discloses a vaccine for preventing SARS-CoV-2 infection, wherein the vaccine comprises an Ad5 adenovirus vector comprising a nucleic acid sequence encoding a SARS-CoV-2 antigen peptide.

The patent document RU2720614 C1 (the National Research Center for Epidemiology and Microbiology named after Honorary Academician N.F. Gamaleya of the Ministry of Health of the Russian Federation) discloses a vaccine based on recombinant adenovirus serotype 5 and/or 26 particles comprising the S protein gene of SARS-CoV-2.

As of the filing date of the present application, the SARS-CoV-2 cases have reached more than 23,000,000 and SARS-CoV-2 deaths have reached more than 800,000. Furthermore, the COVID-19 pandemic still continues at the date of filing of the application. Thus, there is an urgent global need for effective means for the prevention and treatment of diseases caused by the severe acute respiratory syndrome virus SARS-CoV-2.

DESCRIPTION OF INVENTION

The authors of the invention have developed an isolated recombinant receptor-binding domain of the glycoprotein S (RBD-S) of SARS-CoV-2, which is used as an antigen for effective immunization of mammals with the induction of specific immunity to SARS-CoV-2, which fact will contribute to the prevention of SARS-CoV-2-associated diseases. The authors of the invention have also developed a means for delivery of said antigen to a mammalian organism, in particular, an expression vector that includes a nucleic acid encoding said antigen, a recombinant AAV5 (adeno-associated virus serotype 5)-based virus comprising a nucleic acid encoding said antigen, vaccines comprising said objects and methods of their use for the induction of specific immunity to SARS-CoV-2 and/or prevention of SARS-CoV-2-related coronavirus infection.

BRIEF DESCRIPTION OF INVENTION

In one aspect, the present invention relates to an isolated recombinant receptor-binding domain of the glycoprotein (RBD-S) of SARS-CoV-2, which is represented by the amino acid sequence of SEQ ID NO: 1.

In one aspect, the present invention relates to an isolated recombinant receptor-binding domain of the S glycoprotein (RBD-S) of SARS-CoV-2 (severe acute respiratory syndrome-related coronavirus 2), which is represented by the amino acid sequence of SEQ ID NO: 1.

In one aspect, the present invention relates to an isolated nucleic acid that encodes said isolated recombinant receptor-binding domain of the S glycoprotein (RBD-S) of SARS-CoV-2.

In some embodiments, the isolated nucleic acid is DNA.

In some embodiments, the isolated nucleic acid is the nucleotide sequence of SEQ ID NO: 2.

In some embodiments, the isolated nucleic acid is a codon-optimized nucleotide sequence.

In one aspect, the present invention relates to an expression cassette that includes any one of said nucleic acids that encodes said isolated recombinant receptor-binding domain of the S glycoprotein (RBD-S) of SARS-CoV-2.

In some embodiments, the expression cassette includes the following elements in the 5'-end to 3'-end direction:

- a left-hand (first) ITR (inverted terminal repeats);
- a CMV (cytomegalovirus) enhancer;
- a CMV (cytomegalovirus) promoter;
- an intron of the hBG1 gene (hemoglobin subunit gamma 1 gene);
- any one of said nucleic acids that encodes said isolated recombinant receptor-binding domain of the S glycoprotein (RBD-S) of SARS-CoV-2.

an hGH1 polyadenylation signal (human growth hormone gene polyadenylation signal)

a right-hand (second) ITR.

In some embodiments, the expression cassette includes a nucleic acid with SEQ ID NO: 3.

In one aspect, the present invention relates to an expression vector that includes any one of said nucleic acids that encodes said isolated recombinant receptor-binding domain of the S glycoprotein (RBD-S) of SARS-CoV-2, or any one of said expression cassettes.

In one aspect, the present invention relates to an isolated recombinant AAV5 (adeno-associated virus serotype 5)-based virus for the induction of specific immunity to SARS-CoV-2 and/or prevention of the SARS-CoV-2-associated coronavirus infection, which comprises a capsid and any of said expression cassettes.

In some embodiments, the AAV5-based recombinant virus has a capsid that includes the AAV5 protein VP1.

In some embodiments, the AAV5-based recombinant virus has a capsid that includes the AAV protein VP1 having the amino acid sequence of SEQ ID NO: 4.

In some embodiments, the AAV5-based recombinant virus has a capsid that includes the AAV5 protein VP1 having the amino acid sequence of SEQ ID NO: 4 with one or more point mutations.

In some embodiments, the AAV5-based recombinant virus has a capsid that includes the AAV5 protein VP1 having the amino acid sequence of SEQ ID NO: 5 (S2A and T711S).

In some embodiments, the AAV5-based recombinant virus has a capsid that includes the AAV5 protein VP1 having the amino acid sequence of SEQ ID NO: 4 or the amino acid sequence of SEQ ID NO: 4 with one or more point mutations, and the expression cassette includes the following elements in the 5'-end to 3'-end direction:

a left-hand (first) ITR (inverted terminal repeats);

a CMV (cytomegalovirus) enhancer;

a CMV (cytomegalovirus) promoter;

an intron of the hBG1 gene (hemoglobin subunit gamma 1 gene);

any one of said nucleic acids that encodes said isolated recombinant receptor-binding domain of the S glycoprotein (RBD-S) of SARS-CoV-2.

an hGH1 polyadenylation signal (human growth hormone gene polyadenylation signal)

a right-hand (second) ITR.

In some embodiments, the AAV5-based recombinant virus has a capsid that includes the AAV5 protein VP1 having the amino acid sequence of SEQ ID NO: 4 or the amino acid sequence of SEQ ID NO: 4 with one or more point mutations, and the expression cassette comprises a nucleic acid with SEQ ID NO: 3.

In some embodiments, the AAV5-based recombinant virus has a capsid that includes the AAV5 protein VP1 having the amino acid sequence of SEQ ID NO: 4 with one or more point mutations, the AAV5 protein VP1 is the amino acid sequence of SEQ ID NO: 5 (S2A and T711S).

In one aspect, the present invention relates to a pharmaceutical composition for the prevention of SARS-CoV-2-associated coronavirus infection, which comprises any of said recombinant AAV5-based viruses in combination with one or more pharmaceutically acceptable excipients.

In one aspect, the present invention relates to a pharmaceutical composition for the induction of specific immunity to SARS-CoV-2, which comprises any of said recombinant AAV5-based viruses in combination with one or more pharmaceutically acceptable excipients.

In one aspect, the present invention relates to the use of any of said recombinant AAV5-based viruses or said pharmaceutical composition for the prevention of SARS-CoV-2-associated coronavirus infection.

In one aspect, the present invention relates to the use of any of said recombinant AAV5-based viruses or said pharmaceutical composition for the induction of specific immunity to SARS-CoV-2.

In one aspect, the present invention relates to a vaccine for the prevention of SARS-CoV-2-associated coronavirus infection, which comprises any of said recombinant AAV5-based viruses in an effective amount.

In one aspect, the present invention relates to a vaccine for the induction of specific immunity to SARS-CoV-2, which comprises any of said recombinant AAV5-based viruses in an effective amount.

In one aspect, the present invention relates to a method for the induction of specific immunity to SARS-CoV-2, which comprises administering to a mammalian organism any one of said recombinant AAV5-based viruses, said composition or said vaccine for the induction of specific immunity to SARS-CoV-2, in an effective amount.

In one aspect, the present invention relates to a method for preventing SARS-CoV-2-associated coronavirus infection, which comprises administering to a mammalian organism any one of said recombinant AAV5-based viruses, said composition or said vaccine for the prevention of SARS-CoV-2-associated coronavirus infection, in an effective amount.

Leader peptide is a peptide that provides the secretion of the target protein

RBD-S is a recombinant receptor-binding domain of the S glycoprotein of SARS-CoV-2

AmpR is a beta-lactamase gene that provides resistance to ampicillin, pUC origin is a pUC replication origin in bacteria, ITR is inverted terminal repeats, CMV-Enhancer is a cytomegalovirus enhancer, CMV-Promoter is the promoter of cytomegalovirus early genes, Poly A is a polyadenylation signal sequence, for increasing mRNA stability, HBG Intron is human beta globine intron.

Figure 2:
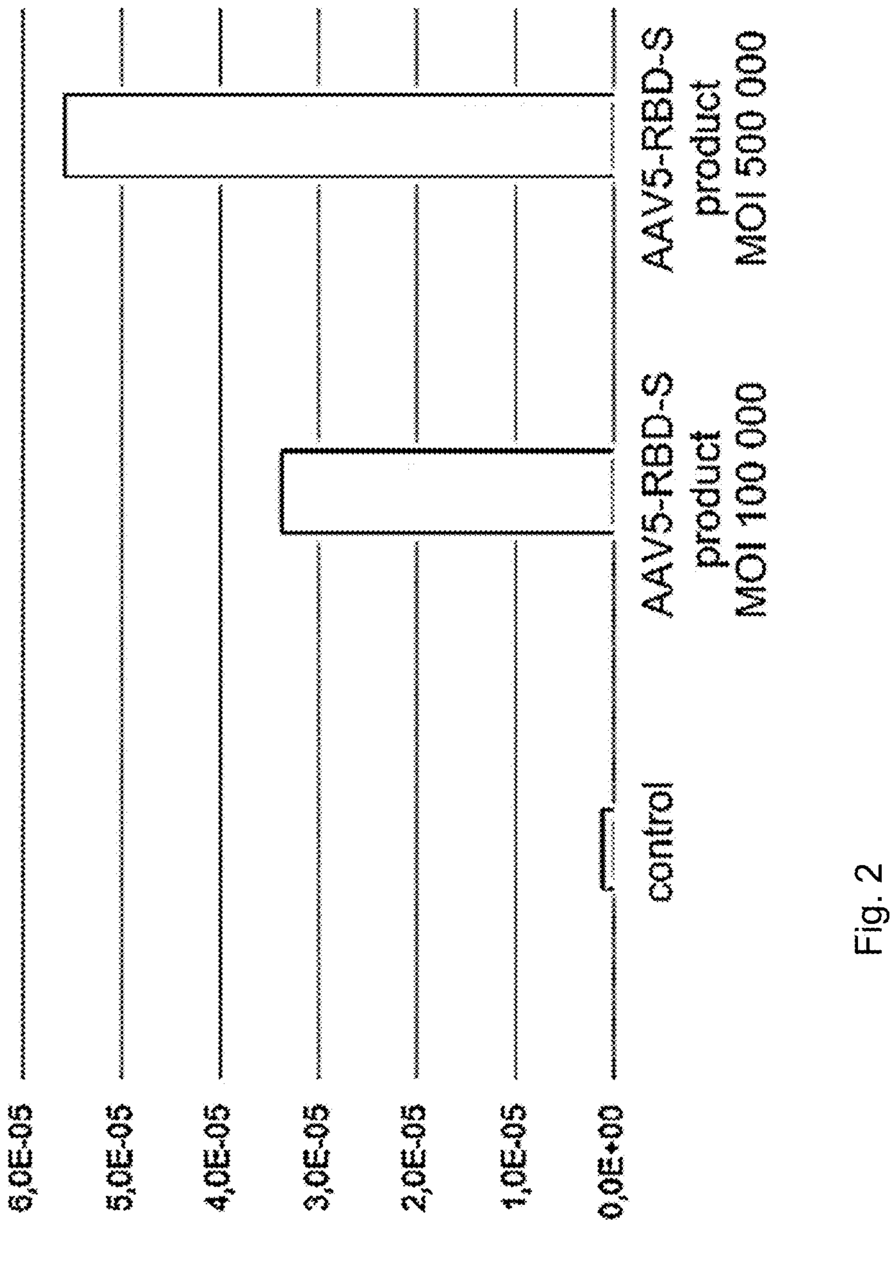

FIG. 2 is a graph showing the concentration of RBD-S protein in CHO-K1-S cell cultures 3 days following cell transduction with the viral AAV5-RBD-S product.

Figure 3:
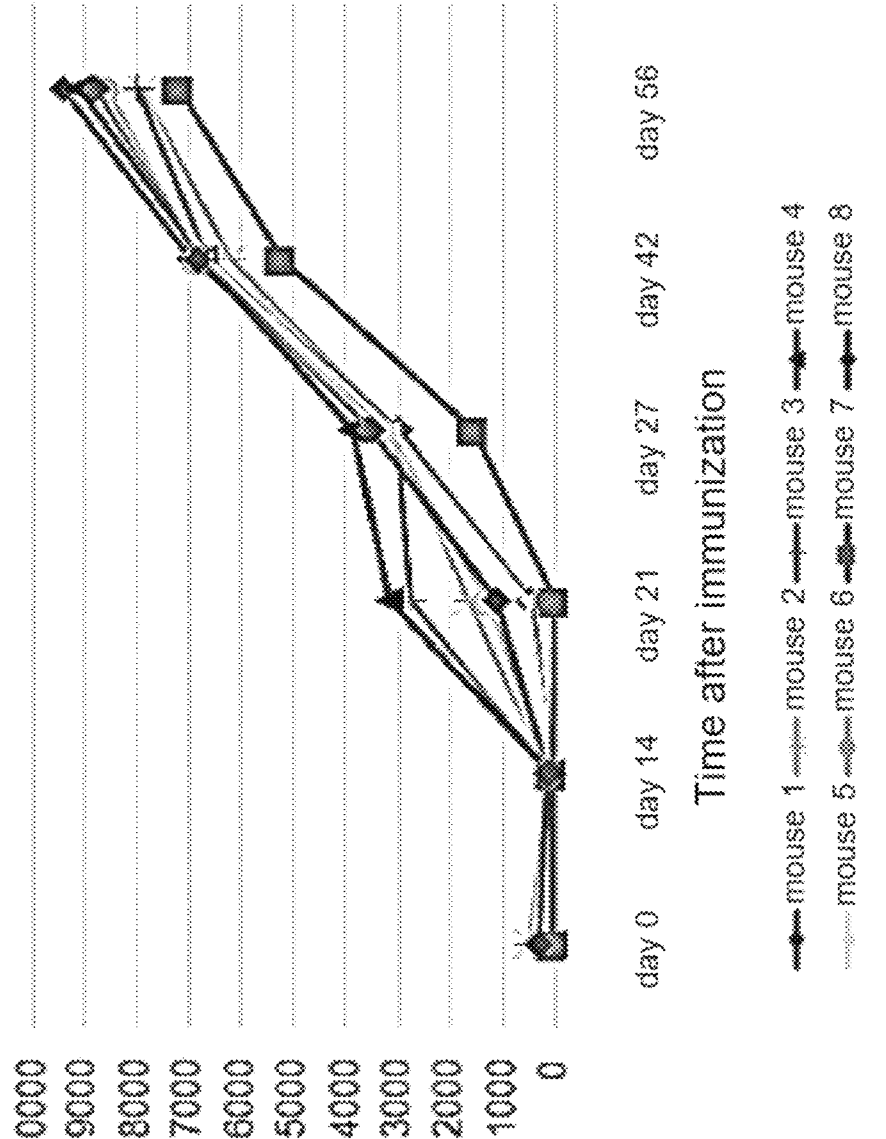
Figure 4:
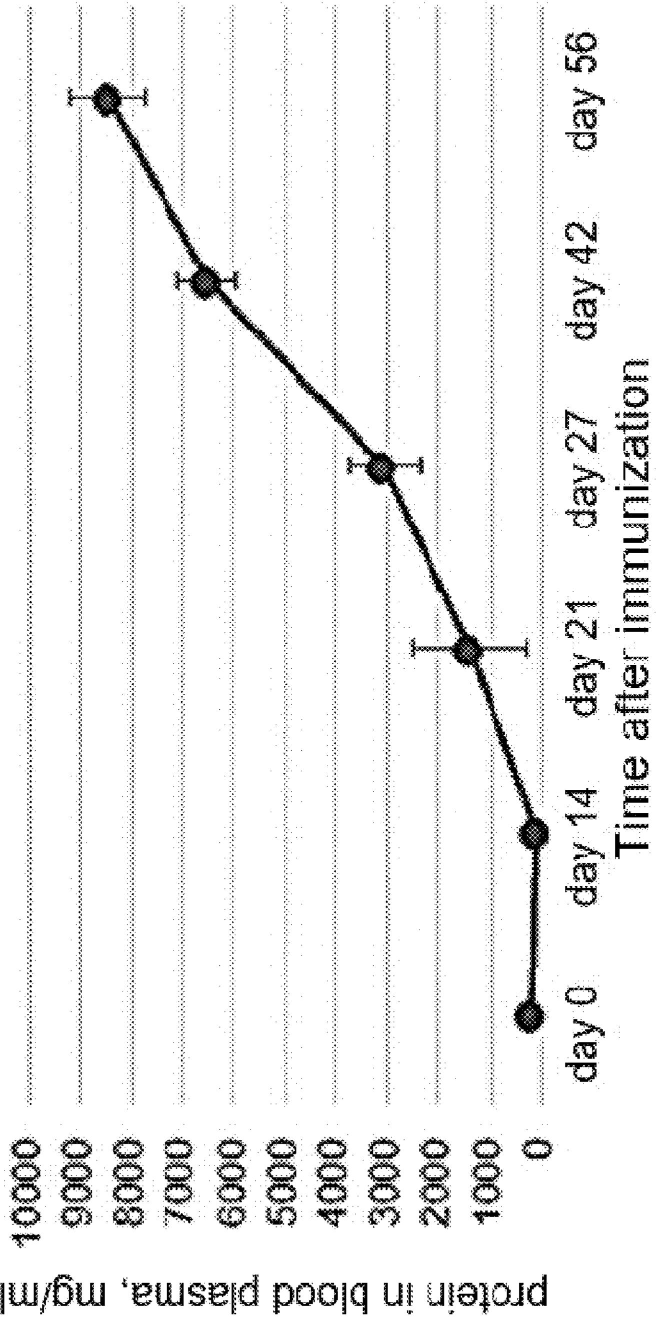

FIG. 3,4 are a graph showing the content of antibodies to the RBD-S protein in the blood plasma of research animals following immunization with the AAV5-RBD-S product (intramuscular injection at $1\times10^{11}$ VG/mouse; injection volume is 200 μl). FIG. 3 is Individual scores for each animal in the study. FIG. 4 is mean values±standard deviation (n=8). VG is viral genomes.

Figure 5:
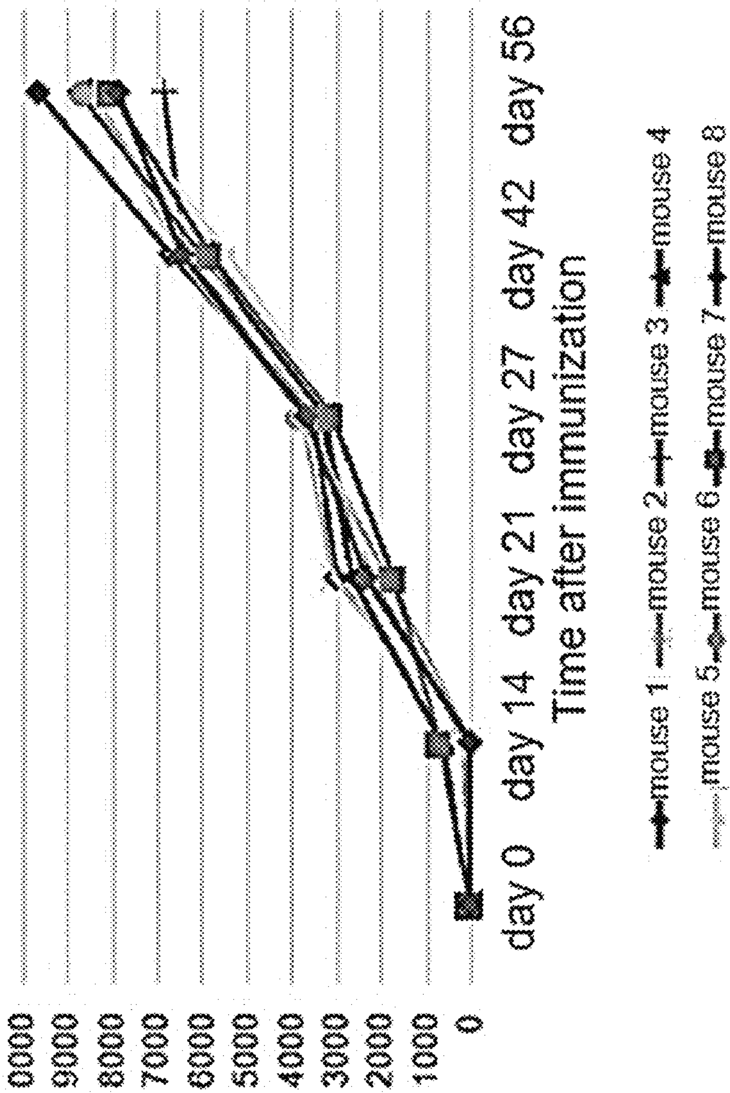
Figure 6:
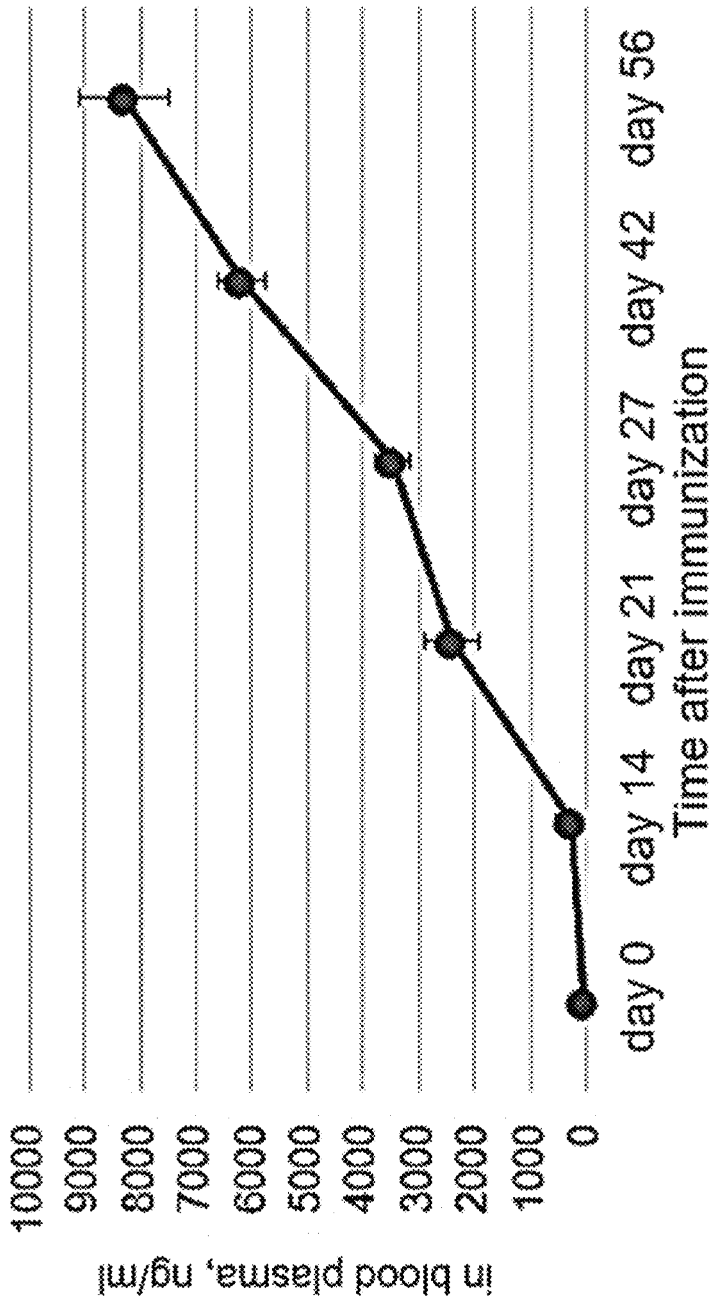

FIG. 5, 6 are a graph showing the content of antibodies to the RBD-S protein in the blood plasma of research animals following immunization with the AAV5-RBD-S product (intramuscular injection at $4\times10^{11}$ VG/mouse; injection volume is 200 μl). FIG. 5 is Individual scores for each animal in the study. FIG. 6 is mean values±standard deviation (n=8). VG is viral genomes.

Figure 7:
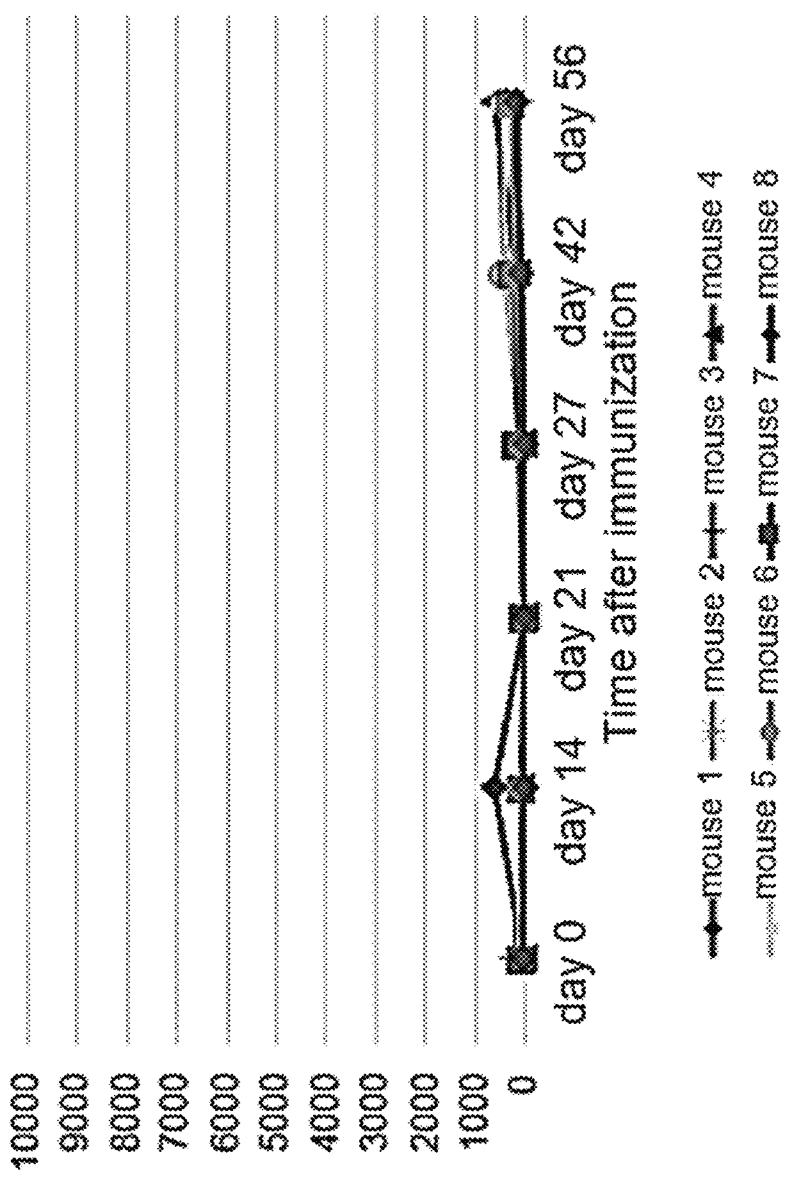

FIG. 7 is a graph showing the content of antibodies to the RBD-S protein in the blood plasma of research animals following immunization with the AAV5 product, the genome of which does not contain an expression cassette with the RBD-S gene (product with empty AAV5 capsids). Intramuscular injection at $8.6\times10^{10}$ CP/mouse; injection volume is 200 μl). The graph shows individual scores for each animal in the study. CP is viral capsids.

Figure 8:
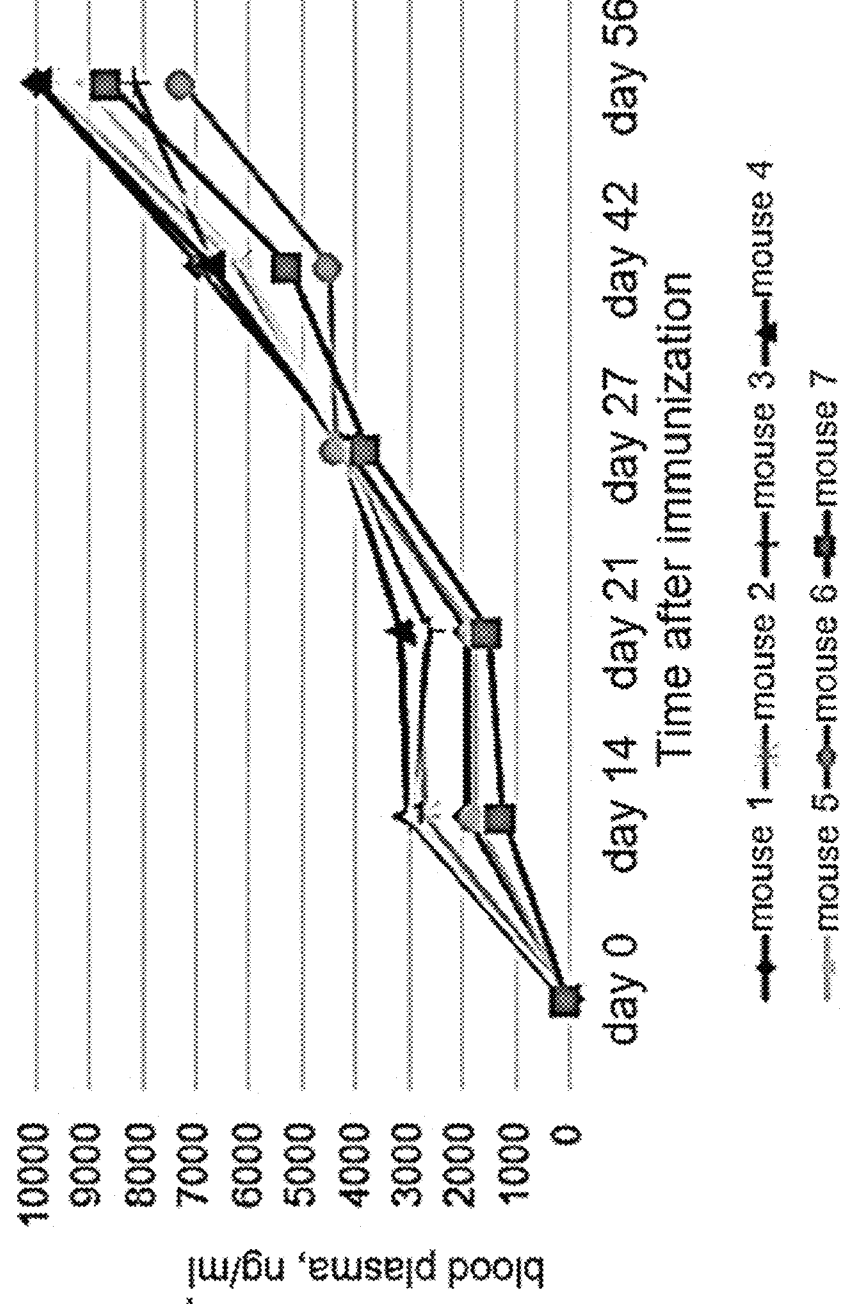
Figure 9:
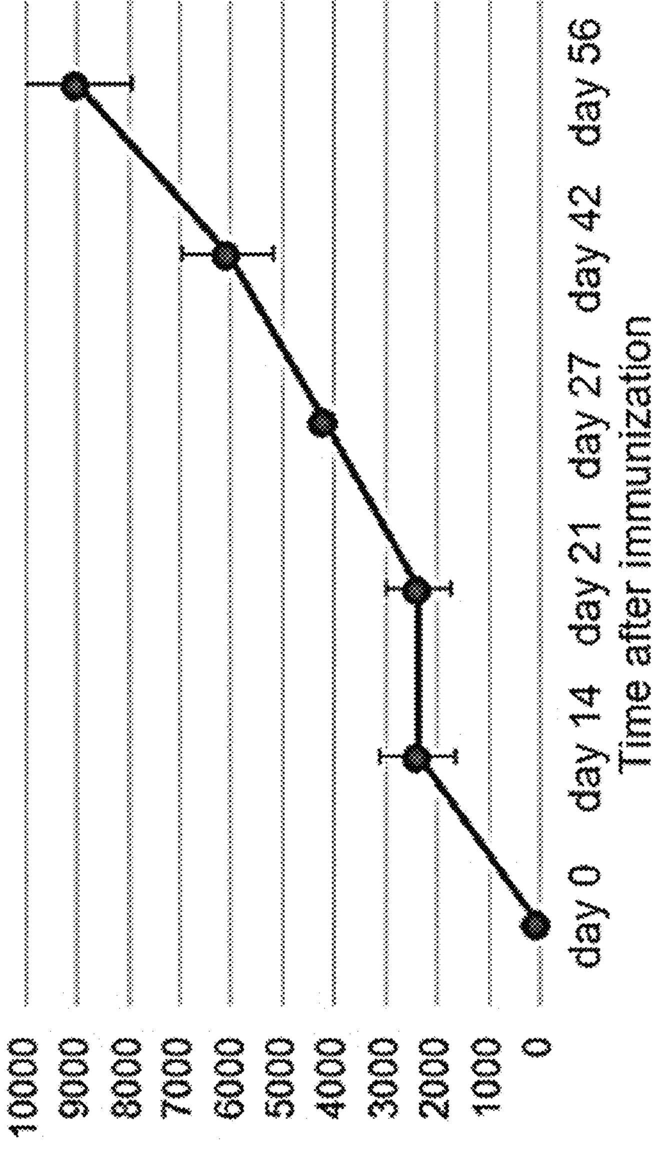

FIG. 8,9 are a graph showing the content of antibodies to the RBD-S protein in the blood plasma of research animals following immunization with the purified recombinant RBD-S protein product (intramuscular injection at 20 μg/mouse). FIG. 8 is Individual scores for each animal in the study. FIG. 9 is mean values±standard deviation (n=7).

Figure 10:
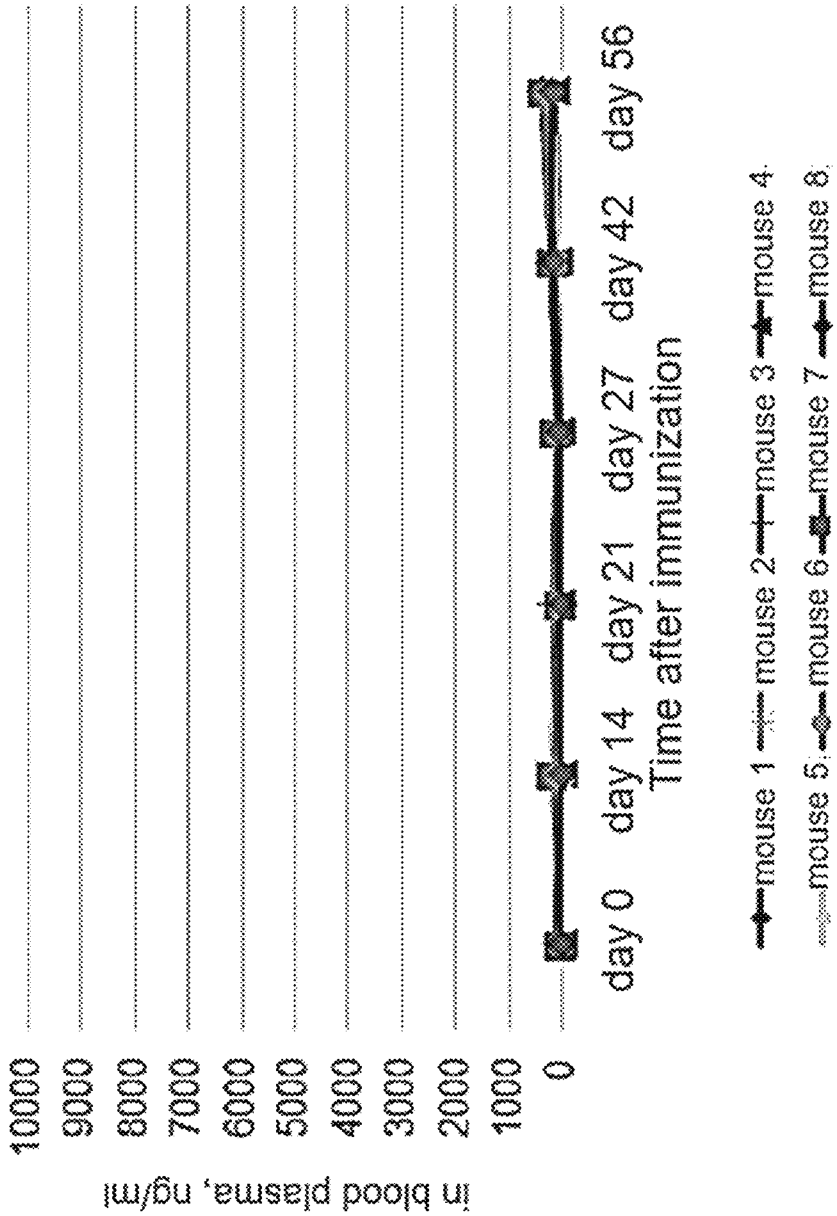

FIG. 10 is a graph showing the content of antibodies to the RBD-S protein in the blood plasma of research animals following immunization with a control AAV-free product. The graph shows individual scores for each animal in the study.

DEFINITIONS AND GENERAL METHODS

Unless defined otherwise, all technical and scientific terms used herein have the same meaning as is commonly understood by one of ordinary skill in the art.

Further, unless otherwise required by context, singular terms shall include pluralities and plural terms shall include the singular terms. Typically, the present classification and methods of cell culture, molecular biology, immunology, microbiology, genetics, analytical chemistry, organic synthesis chemistry, medical and pharmaceutical chemistry, as well as hybridization and chemistry of protein and nucleic acids described herein are well known by those skilled and widely used in the art. Enzyme reactions and purification methods are performed according to the manufacturer's guidelines, as is common in the art, or as described herein.

"Isolated" means altered or removed from the natural state. For example, a nucleic acid or a peptide naturally present in an animal is not "isolated", but the same nucleic acid or peptide partially or completely separated from the coexisting materials of its natural state is "isolated". An isolated nucleic acid or protein can exist in substantially purified form, or can exist in a non-native environment such as, for example, a genetically modified cell.

The terms "naturally occurring," "native," or "wild-type" is used to describe an object that can be found in nature as distinct from being artificially produced. For example, a protein or nucleotide sequence present in an organism (including a virus), which can be isolated from a source in nature and that has not been intentionally modified by a person in the laboratory, is naturally occurring.

The term "genome" refers to the complete genetic material of an organism.

As used in the present description and claims that follow, unless otherwise dictated by the context, the words "include" and "comprise," or variations thereof such as "having," "includes", "including", "comprises," or "comprising," will be understood to imply the inclusion of a stated integer or group of integers but not the exclusion of any other integer or group of integers.

Protein (Peptide)

As used in the present description, the terms "peptide", "polypeptide" and "protein" are used interchangeably, and they refer to a compound consisting of amino acid residues that are covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used in the present description, the term refers to both short chains, which also commonly are referred to in the art, for example, as peptides, oligopeptides and oligomers, and to longer chains, which generally are referred to in the art as proteins, of which there are many types. "Polypeptides" include, inter alia, for example, biologically active fragments, substantially homologous polypeptides, oligopeptides, homodimers, heterodimers, variants of polypeptides, modified polypeptides, derivatives, analogs, fusion proteins. The polypeptides include natural peptides, recombinant peptides, synthetic peptides, or a combination thereof.

Nucleic Acid Molecules

The terms "nucleic acid", "nucleic sequence", "nucleic acid sequence", "polynucleotide", "oligonucleotide", "polynucleotide sequence" and "nucleotide sequence", used interchangeably in the present description, mean a precise sequence of nucleotides, modified or not, determining a fragment or a region of a nucleic acid, containing unnatural nucleotides or not, and being either a double-stranded DNA or RNA, a single-stranded DNA or RNA, or transcription products of said DNAs.

One skilled in the art has the general knowledge that nucleic acids are polynucleotides that can be hydrolyzed to monomeric "nucleotides". Monomeric nucleotides can be hydrolyzed into nucleosides. As used in the present description, polynucleotides include, as non-limiting examples, all nucleic acid sequences which are obtained by any means available in the art, including, as non-limiting examples, recombinant means, i.e. the cloning of nucleic acid sequences from a recombinant library or a cell genome, using ordinary cloning technology and PCR and the like, and by synthetic means.

It should also be noted here that the present invention does not relate to nucleotide sequences in their natural chromosomal environment, i.e. in a natural state. The sequences of the present invention have been isolated and/or purified, i.e. they were sampled directly or indirectly, for example by a copy, their environment having been at least partially modified. Thus, isolated nucleic acids obtained by recombinant genetics, by means, for example, of host cells, or obtained by chemical synthesis should also be mentioned here.

Unless otherwise indicated, the term nucleotide sequence encompasses its complement. Thus, a nucleic acid having a particular sequence should be understood as one which encompasses the complementary strand thereof with the complementary sequence thereof.

The terms "transformation," "transfection," and "transduction" refer to any method or means by which a nucleic acid is introduced into a cell or host organism, and may be used interchangeably to convey the same meaning. Such methods include, but are not limited to, transfection, electroporation, microinjection, infection, PEG-fusion, and the like.

Adeno-Associated Virus (AAV)

Viruses of the Parvoviridae family are small DNA-containing animal viruses. The Parvoviridae family may be divided into two subfamilies: the Parvovirinae, which members infect vertebrates, and the Densovirinae, which members infect insects. By 2006, there have been 11 serotypes of adeno-associated virus described (Mori, S. ET AL., 2004, «Two novel adeno-associated viruses from cynomolgus monkey: pseudotyping characterization of capsid protein», Virology, T. 330 (2): 375-83). All of the known serotypes can infect cells from multiple tissue types. Tissue specificity is determined by the capsid protein serotype; therefore, the adeno-associated virus-based vectors are constructed by assigning the desired serotype. Further information on parvoviruses and other members of the Parvoviridae is described in the literature (Kenneth I. Berns, «Parvoviridae: The Viruses and Their Replication», Chapter 69 in Fields Virology (3d Ed. 1996)).

The genomic organization of all known AAV serotypes is very similar. The genome of AAV is a linear, single-stranded DNA molecule that is less than about 5000 nucleotides (nt) in length. Inverted terminal repeats (ITRs) flank the unique coding nucleotide sequences of replication of non-structural proteins (Rep) and structural proteins (Cap). The Cap gene encodes the VP proteins (VP1, VP2, and VP3) which form the capsid. The terminal 145 nucleotides are self-complementary and are organized such that an energetically stable intramolecular duplex forming a T-shaped hairpin may be formed. Such hairpin structures function as an origin for virus DNA replication, serving as primers for the cellular DNA polymerase complex. Following wild-type AAV (wtAAV) infection in mammalian cells, the Rep genes (e.g. Rep78 and Rep52) are expressed using the P5 promoter and the P19 promoter, respectively, and the both Rep proteins have a certain function in the replication of the viral genome. A splicing event in the Rep open reading frame (Rep ORF) results in the expression of actually four Rep proteins (e.g. Rep78, Rep68, Rep52, and Rep40). However, it has been shown that the unspliced mRNA encoding Rep78 and Rep52 proteins is sufficient for AAV vector production in mammalian cells.

Vector

The term "vector" as used herein means a nucleic acid molecule capable of transporting another nucleic acid to which it has been linked.

The terms "infection unit (iu)," "infectious particle," or "replication unit," as used in reference to a viral titer, refer to the number of infectious recombinant AAV vector particles as measured by the infectious center assay, also known as replication center assay, as described, for example, in McLaughlin et al., J. Virol. (1988) 62:1963-1973.

The term "heterologous" as it relates to nucleic acid sequences such as coding sequences and regulatory sequences, denotes sequences that are not normally joined together, and/or are not normally associated with a particular cell. Thus, a "heterologous" region of a nucleic acid construct or a vector is a fragment of nucleic acid within or attached to another nucleic acid molecule that is not found in association with the other molecule in nature. For example, a heterologous region of a nucleic acid construct may include a coding sequence flanked by sequences not found in association with the coding sequence in nature. Another example of a heterologous coding sequence is a construct where the coding sequence itself is not found in nature (e.g. synthetic sequences having codons different from the native gene).

As used in the present description, the term "expression" is defined as the transcription and/or translation of a particular nucleotide sequence driven by its promoter.

Use

The term "prophylaxis" or "prevention" and the like means slowing down or preventing the onset of symptoms of a disease, disorder or infection.

The term "induction of an immune response" as used in the present invention refers to the specific control of or effect on the activity of the immune response and includes activation of an immune response, stimulation of an immune response, enhancement of an immune response.

The term "specific immunity" as used in the present invention refers to a condition of being immune to disease after the induction of an immune response.

The term "disorder" means any condition that would benefit from treatment according to the present invention. This includes chronic and acute disorders or diseases including those pathological conditions that predispose the mammal to the disorder in question.

"Disease" is a state of health of an animal where the animal cannot maintain homeostasis, and where if the disease is not ameliorated then the animal's health continues to deteriorate.

The terms "subject," "patient," "individual," and the like are used interchangeably in the present description, and they refer to any animal amenable to the methods described in the present description. In certain non-limiting embodiments, the subject, patient or individual is a human. Said subject may be either male or female, of any age.

"Therapeutically effective amount" or "effective amount" refers to that amount of the therapeutic agent being administered which will relieve to some extent one or more of the symptoms of the disease being prevented.

DETAILED DESCRIPTION OF INVENTION

Peptidic Antigen

In one aspect, the present invention relates to an isolated recombinant receptor-binding domain of the glycoprotein (RBD-S) of SARS-CoV-2 (severe acute respiratory syndrome-related coronavirus 2), which is represented by the amino acid sequence (SEQ ID NO: 1)

```
RVQPTESIVRFPNITNLCPFGEVFNATRFASVYAWNRKRISNCVADYSVL

YNSASFSTFKCYGVSPTKLNDLCFTNVYADSFVIRGDEVRQIAPGQTGKI

ADYNYKLPDDFTGCVIAWNSNNLDSKVGGNYNYLYRLFRKSNLKPFERDI

STEIYQAGSTPCNGVEGFNCYFPLQSYGFQPTNGVGYQPYRVVVLSFELL

HAPATVCGPKKSTNLVKNKCVNFNFNGLTGTGVLTESNKKFLPFQQFGRD

IADTTDAVRDPQTLEILDITPSSFGGVS.
```

Said RBD-S of SARS-CoV-2 was obtained from a full length S glycoprotein of SARS-CoV-2, which have been described in the GenBank database, Wu F., Severe acute respiratory syndrome coronavirus 2 isolate Wuhan-Hu-1, complete genome, 2020, GenBank: MN908947.3 and in Fan Wu ET AL., A new coronavirus associated with human respiratory disease in China, 2020, Nature, volume 579, pages 265-269 and has the following amino acid sequence:

(SEQ ID NO: 6)

```
MFVFLVLLPLVSSQCVNLTTRTQLPPAYTNSFTRGVYYPDKVFRSSVLHS

TQDLFLPFFSNVTWFHAIHVSGTNGTKRFDNPVLPFNDGVYFASTEKSNI

IRGWIFGTTLDSKTQSLLIVNNATNVVIKVCEFQFCNDPFLGVYYHKNNK

SWMESEFRVYSSANNCTFEYVSQPFLMDLEGKQGNFKNLREFVFKNIDGY

FKIYSKHTPINLVRDLPQGFSALEPLVDLPIGINITRFQTLLALHRSYLT

PGDSSSGWTAGAAAYYVGYLQPRTFLLKYNENGTITDAVDCALDPLSETK
```

-continued

```
CTLKSFTVEKGIYQTSNFRVQPTESIVRFPNITNLCPFGEVFNATRFASV
YAWNRKRISNCVADYSVLYNSASFSTFKCYGVSPTKLNDLCFTNVYADSF
VIRGDEVRQIAPGQTGKIADYNYKLPDDFTGCVIAWNSNNLDSKVGGNYN
YLYRLFRKSNLKPFERDISTEIYQAGSTPCNGVEGFNCYFPLQSYGFQPT
NGVGYQPYRVVVLSFELLHAPATVCGPKKSTNLVKNKCVNFNFNGLTGTG
VLTESNKKFLPFQQFGRDIADTTDAVRDPQTLEILDITPCSFGGVSVITP
GTNTSNQVAVLYQDVNCTEVPVAIHADQLTPTWRVYSTGSNVFQTRAGCL
IGAEHVNNSYECDIPIGAGICASYQTQTNSPRRARSVASQSIIAYTMSLG
AENSVAYSNNSIAIPTNFTISVTTEILPVSMTKTSVDCTMYICGDSTECS
NLLLQYGSFCTQLNRALTGIAVEQDKNTQEVFAQVKQTYKTPPIKDFGGF
NFSQILPDPSKPSKRSFIEDLLFNKVTLADAGFIKQYGDCLGDIAARDLI
CAQKFNGLTVLPPLLTDEMIAQYTSALLAGTITSGWTFGAGAALQIPFAM
QMAYRENGIGVTQNVLYENQKLIANQFNSAIGKIQDSLSSTASALGKLQD
VVNQNAQALNTLVKQLSSNFGAISSVLNDILSRLDKVEAEVQIDRLITGR
LQSLQTYVTQQLIRAAEIRASANLAATKMSECVLGQSKRVDFCGKGYHLM
SFPQSAPHGVVFLHVTYVPAQEKNFTTAPAICHDGKAHFPREGVFVSNGT
HWFVTQRNFYEPQIITTDNTFVSGNCDVVIGIVNNTVYDPLQPELDSFKE
ELDKYFKNHTSPDVDLGDISGINASVVNIQKEIDRLNEVAKNLNESLIDL
QELGKYEQYIKWPWYIWLGFIAGLIAIVMVTIMLCCMTSCCSCLKGCCSC
GSCCKFDEDDSEPVLKGVKLHYT.
```

A receptor-binding domain of the S glycoprotein (RBD-S) of SARS-CoV-2 was selected from said sequence of the S glycoprotein of SARS-CoV-2 based on the analysis of the structure of this glycoprotein (see Example 1), the receptor-binding domain of the S glycoprotein of SARS-CoV-2 having the following amino acid sequence

```
                                      (SEQ ID NO: 7)
RVQPTESIVRFPNITNLCPFGEVFNATRFASVYAWNRKRISNCVADYSV
LYNSASFSTEKCYGVSPTKLNDLCFTNVYADSFVIRGDEVRQIAPGQTG
KIADYNYKLPDDFTGCVIAWNSNNLDSKVGGNYNYLYRLFRKSNLKPFE
RDISTEIYQAGSTPCNGVEGFNCYFPLQSYGFQPTNGVGYQPYRVVVLS
FELLHAPATVCGPKKSTNLVKNKCVNFNFNGLTGTGVLTESNKKFLPFQ
QFGRDIADTTDAVRDPQTLEILDITPCSFGGVS.
```

Next, a point amino acid substitution C272S was introduced into the amino acid sequence with SEQ ID NO: 7 to provide additional stability of the RBD-S protein of SARS-CoV-2 to thereby produce the recombinant receptor-binding domain of the S glycoprotein (RBD-S) of SARS-CoV-2 with the amino acid sequence of SEQ ID NO: 1.

Nucleic Acid

In one aspect, the present invention relates to an isolated nucleic acid that encodes said isolated recombinant receptor-binding domain of the S glycoprotein (RBD-S) of SARS-CoV-2.

An "isolated" nucleic acid molecule is one which is identified and separated from at least one nucleic acid molecule-impurity, which the former is typically bound to in the natural source of nuclease nucleic acid. An isolated nucleic acid molecule is different from the form or set in which it is found under natural conditions. Thus, an isolated nucleic acid molecule is different from a nucleic acid molecule that exists in cells under natural conditions. An isolated nucleic acid molecule however includes a nucleic acid molecule located in cells in which the nuclease is normally expressed, for example, if the nucleic acid molecule has a chromosomal localization that is different from its localization in cells under natural conditions.

In some embodiments, the isolated nucleic acid is DNA.

In some embodiments, the isolated nucleic acid is the nucleotide sequence

```
                                      (SEQ ID NO: 2)
AGAGTCCAACCAACAGAATCTATTGTTAGATTTCCTAATATTACAAACT
TGTGCCCTTTTGGTGAAGTTTTTAACGCCACCAGATTTGCATCTGTTTA
TGCTTGGAACAGGAAGAGAATCAGCAACTGTGTTGCTGATTATTCTGTC
CTATATAATTCCGCATCATTTTCCACTTTTAAGTGTTATGGAGTGTCTC
CTACTAAATTAAATGATCTCTGCTTTACTAATGTCTATGCAGATTCATT
TGTAATTAGAGGTGATGAAGTCAGACAAATCGCTCCAGGGCAAACTGGA
AAGATTGCTGATTATAATTATAAATTACCAGATGATTTTACAGGCTGCG
TTATAGCTTGGAATTCTAACAATCTTGATTCTAAGGTTGGTGGTAATTA
TAATTACCTGTATAGATTGTTTAGGAAGTCTAATCTCAAACCTTTTGAG
AGAGATATTTCAACTGAAATCTATCAGGCCGGTAGCACACCTTGTAATG
GTGTTGAAGGTTTTAATTGTTACTTTCCTTTACAATCATATGGTTTCCA
ACCCACTAATGGTGTTGGTTACCAACCATACAGAGTAGTAGTACTTTCT
TTTGAACTTCTACATGCACCAGCAACTGTTTGTGGACCTAAAAAGTCTA
CTAATTTGGTTAAAAACAAATGTGTCAATTTCAACTTCAATGGTTTAAC
AGGCACAGGTGTTCTTACTGAGTCTAACAAAAAGTTTCTGCCTTTCCAA
CAATTTGGCAGAGACATTGCTGACACTACTGATGCTGTCCGTGATCCAC
AGACACTTGAGATTCTTGACATTACACCATCTTCTTTTGGTGGTGTCAG
T.
```

In some embodiments, the isolated nucleic acid is a codon-optimized nucleotide sequence.

Expression cassette. Expression vector. In one aspect, the present invention relates to an expression cassette that includes any one of said nucleic acids that encodes said isolated recombinant receptor-binding domain of the S glycoprotein (RBD-S) of SARS-CoV-2.

The term "expression cassette", as used herein, refers in particular to a DNA fragment that is capable, in an appropriate setting, of triggering the expression of a polynucleotide encoding a polypeptide of interest that is included in said expression cassette. When introduced into a host cell, the expression cassette is, inter alia, capable of engaging cellular mechanisms to transcribe the polynucleotide encoding the polypeptide of interest into RNA that is then typically further processed and eventually translated into the polypeptide of interest. The expression cassette may be contained in an expression vector.

The expression cassette of the present invention comprises a promoter as an element. The term "promoter" as used herein refers in particular to a DNA element that promotes the transcription of a polynucleotide to which the promoter is operably linked. The promoter may further form part of a promoter/enhancer element. Although the physical boundaries between the "promoter" and "enhancer" elements are not always clear, the term "promoter" typically refers to a site on the nucleic acid molecule to which an RNA polymerase and/or any associated factors binds and at which transcription is initiated. Enhancers potentiate promoter activity temporally as well as spatially. Many promoters are known in the art to be transcriptionally active in a wide range of cell types. Promoters can be divided into two classes, those that function constitutively and those that are regulated by induction or derepression. The both classes are suitable for protein expression. Promoters that are used for high-level production of polypeptides in eukaryotic cells and, in particular, in mammalian cells, should be strong and preferably active in a wide range of cell types. Strong constitutive promoters which are capable of driving expression in many cell types are well known in the art and, therefore, it is not herein necessary to describe them in detail. In accordance with the idea of the present invention, it is preferable to use the cytomegalovirus (CMV) promoter. A promoter or promoter/enhancer derived from the immediate early (IE) region of human cytomegalovirus (hCMV) is particularly suitable as a promoter in the expression cassette of the present invention. The immediate early (IE) region of human cytomegalovirus (hCMV) and obtained therefrom functional expression-inducing fragments and/or functional expression-augmenting fragments, for example, are described in EP0173177 and EP0323997 and are also well known in the art. Thus, several fragments of the immediate early (IE) region of hCMV may be used as a promoter and/or promoter/enhancer. According to one embodiment of the invention, the human CMV promoter is used in the expression cassette of the present invention.

In some embodiments, the expression cassette includes the following elements in the 5'-end to 3'-end direction:

a left-hand (first) ITR (inverted terminal repeats);

a CMV (cytomegalovirus) enhancer;

a CMV (cytomegalovirus) promoter;

an intron of the hBG1 gene (hemoglobin subunit gamma 1 gene);

any one of said nucleic acids that encodes said isolated recombinant receptor-binding domain of the S glycoprotein (RBD-S) of SARS-CoV-2.

an hGH1 polyadenylation signal (human growth hormone gene polyadenylation signal)

a right-hand (second) ITR.

In some embodiments, the left-hand (first) ITR (inverted terminal repeats) has the following nucleic acid sequence:

```
                                         (SEQ ID NO: 8)
Cctgcaggcagctgcgcgctcgctcgctcactgaggccgcccgggcgtc

ggggatttggtcgcccggcctcagtgagcgagcgagcgcgcagagaggg

agtggccaactccatcactaggggttcct.
```

In some embodiments, the CMV (cytomegalovirus) enhancer has the following nucleic acid sequence:

```
                                         (SEQ ID NO: 9)
cgttacataacttacggtaaatggcccgcctggctgaccgcccaacgac

ccccgcccattgacgtcaataatgacgtatgttcccatagtaacgCcaa

tagggactttccattgacgtcaatgggtggagtatttacggtaaactgc

ccacttggcagtacatcaagtgtatcatatgccaagtacgccccctatt
```

-continued

```
gacgtcaatgacggtaaatggcccgcctggcattatgcccagtacatga

ccttatgggactttcctacttggcagtacatctacgtattagtcatcgc

tattaccatg.
```

In some embodiments, the CMV (cytomegalovirus) promoter has the following nucleic acid sequence:

```
                                        (SEQ ID NO: 10)
gtgatgcggttttggcagtacatcaatgggcgtggatagcggtttgact

cacggggatttccaagtctccaccccattgacgtcaatgggagtttgtt

ttgGcaccaaaatcaacgggactttccaaaatgtcgtaacaactccgcc

ccattgacgcaaatgggcggtaggcgtgtacggtgggaggtctatataa

gcagagct.
```

In some embodiments, the intron of the hBG1 (hemoglobin subunit gamma 1) gene has the following nucleic acid sequence:

```
                                        (SEQ ID NO: 11)
cgaatcccggccgggaacggtgcattggaacgcggattccccgtgccaa

gagtgacgtaagtaccgcctatagagtctataggcccacaaaaaatgct

ttcttcttttaatatacttttttgtttatcttatttctaatactttccc

taatctctttctttcagggcaataatgatacaatgtatcatgcctcttt

gcaccattctaaagaataacagtgataatttctgggttaaggcaatagc

aatatttctgcatataaatatttctgcatataaattgtaactgatgtaa

gaggtttcatattgctaatagcagctacaatccagctaccattctgctt

ttattttatggttgggataaggctggattattctgagtccaagctaggc

ccttttgctaatcatgttcatacctcttatcttcctcccacagctcctg

ggcaacgtgctggtctgtgtgctggcccatcactttggcaaagaattgg

gat.
```

In some embodiments, the hGH1 (human growth hormone 1 gene) polyadenylation signal has the following nucleic acid sequence:

```
                                        (SEQ ID NO: 12)
Acgggtggcatccctgtgacccctccccagtgcctctcctggccctgga

agttgccactccagtgcccaccagccttgtcctaataaaattaagttgc

atcattttgtctgactaggtgtccttctataatattatggggtggaggg

gggtggtatggagcaaggggcaagttgggaagacaacctgtagggcctg

cggggtctattgggaaccaagctggagtgcagtggcacaatcttggctc

actgcaatctccgcctcctgggttcaagcgattctcctgcctcagcctc

ccgagttgttgggattccaggcatgcatgaccaggctcagctaatttttt

tttttttggtagagacggggtttcaccatattggccaggctggtctcca

actcctaatctcaggtgatctacccaccttggcctcccaaattgctggg

attacaggcgtgaaccactgctcccttccctgtcctt.
```

In some embodiments, the right-hand (second) ITR has the following nucleic acid sequence:

```
                                         (SEQ ID NO: 13)
aggaacccctagtgatggagttggccactccctctctgcgcgctcgctc

gctcactgagcgcgcagctgcctgcagg.
```

In some embodiments, the expression cassette includes a nucleic acid with the nucleotide sequence:

```
                                          (SEQ ID NO: 3)
cctgcaggcagctgcgcgctcgctcgctcactgaggccgcccgggcgtc

ggggacctttggtcgcccggcctcagtgagcgagcgagcgcgcagagag

ggagtggccaactccatcactaggggttcctgcggccgcacgcgtctag

ttattaatagtaatcaattacggggtcattagttcatagcccatatatg

gagttccgcgttacataacttacggtaaatggcccgcctggctgaccgc

ccaacgacccccgcccattgacgtcaataatgacgtatgttcccatagt

aacgCcaatagggactttccattgacgtcaatgggtggagtatttacgg

taaactgcccacttggcagtacatcaagtgtatcatatgccaagtacgc

cccctattgacgtcaatgacggtaaatggcccgcctggcattatgccca

gtacatgaccttatgggactttcctacttggcagtacatctacgtatta

gtcatcgctattaccatggtgatgcggttttggcagtacatcaatgggc

gtggatagcggtttgactcacggggatttccaagtctccaccccattga

cgtcaatgggagtttgttttgGcaccaaaatcaacgggactttccaaaa

tgtcgtaacaactccgccccattgacgcaaatgggcggtaggcgtgtac

ggtgggaggtctatataagcagagctcgtttagtgaaccgtcagatcgc

ctggagacgccatccacgctgttttgacctccatagaagacaccgggac

cgatccagcctccgcggattcgaatcccggccgggaacggtgcattgga

acgcggattccccgtgccaagagtgacgtaagtaccgcctatagagtct

ataggcccacaaaaaatgctttcttcttttaatatacttttttgtttat

cttatttctaatactttccctaatctctttctttcagggcaataatgat

acaatgtatcatgcctctttgcaccattctaaagaataacagtgataat

ttctgggttaaggcaatagcaatatttctgcatataaatatttctgcat

ataaattgtaactgatgtaagaggtttcatattgctaatagcagctaca

atccagctaccattctgcttttattttatggttgggataaggctggatt

attctgagtccaagctaggcccttttgctaatcatgttcatacctctta

tcttcctcccacagctcctgggcaacgtgctggtctgtgtgctggccca

tcactttggcaaagaattgggattcgaacatcgCGATaattaGCCGCCA

CCATGGAGACCGACACCCTGCTGCTGTGGGTGCTGCTGCTGTGGGTGCC

CGGGTCGACCGGGAGAGTCCAACCAACAGAATCTATTGTTAGATTTCCT

AATATTACAAACTTGTGCCCTTTTGGTGAAGTTTTTAACGCCACCAGAT

TTGCATCTGTTTATGCTTGGAACAGGAAGAGAATCAGCAACTGTGTTGC

TGATTATTCTGTCCTATATAATTCCGCATCATTTTCCACTTTTAAGTGT

TATGGAGTGTCTCCTACTAAATTAAATGATCTCTGCTTTACTAATGTCT
```

-continued

```
ATGCAGATTCATTTGTAATTAGAGGTGATGAAGTCAGACAAATCGCTCC

AGGGCAAACTGGAAAGATTGCTGATTATAATTATAAATTACCAGATGAT

TTTACAGGCTGCGTTATAGCTTGGAATTCTAACAATCTTGATTCTAAGG

TTGGTGGTAATTATAATTACCTGTATAGATTGTTTAGGAAGTCTAATCT

CAAACCTTTTGAGAGAGATATTTCAACTGAAATCTATCAGGCCGGTAGC

ACACCTTGTAATGGTGTTGAAGGTTTTAATTGTTACTTTCCTTTACAAT

CATATGGTTTCCAACCCACTAATGGTGTTGGTTACCAACCATACAGAGT

AGTAGTACTTTCTTTTGAACTTCTACATGCACCAGCAACTGTTTGTGGA

CCTAAAAAGTCTACTAATTTGGTTAAAAACAAATGTGTCAATTTCAACT

TCAATGGTTTAACAGGCACAGGTGTTCTTACTGAGTCTAACAAAAAGTT

TCTGCCTTTCCAACAATTTGGCAGAGACATTGCTGACACTACTGATGCT

GTCCGTGATCCACAGACACTTGAGATTCTTGACATTACACCATCTTCTT

TTGGTGGTGTCAGTtaaGgatcctctagagtcgacctgcagaagcttgc

ctcgagcagcgctgctcgagagatctacgggtggcatccctgtgacccc

tccccagtgcctctcctggccctggaagttgccactccagtgcccacca

gccttgtcctaataaaattaagttgcatcattttgtctgactaggtgtc

cttctataatattatggggtggaggggggtggtatggagcaaggggcaa

gttgggaagacaacctgtagggcctgcggggtctattgggaaccaagct

ggagtgcagtggcacaatcttggctcactgcaatctccgcctcctgggt

tcaagcgattctcctgcctcagcctcccgagttgttgggattccaggca

tgcatgaccaggctcagctaatttttgtttttttggtagagacggggtt

tcaccatattggccaggctggtctccaactcctaatctcaggtgatcta

cccaccttggcctcccaaattgctgggattacaggcgtgaaccactgct

cccttccctgtccttctgattttgtaggtaaccacgtgcggaccgagcg

gccgcaggaacccctagtgatggagttggccactccctctctgcgcgct

cgctcgctcactgaggccgggcgaccaaaggtg.
```

In one aspect, the present invention relates to an expression vector that includes any one of said nucleic acids that encodes said isolated recombinant receptor-binding domain of the S glycoprotein (RBD-S) of SARS-CoV-2, or any one of said expression cassettes.

In some embodiments, the vector is a plasmid, i.e., a circular double stranded piece of DNA into which additional DNA segments may be ligated.

In some embodiments, the vector is a viral vector, wherein additional DNA segments may be ligated into the viral genome.

In some embodiments, vectors are capable of autonomous replication in a host cell into which they are introduced (e.g. bacterial vectors having a bacterial origin site of replication and episomal mammalian vectors). In further embodiments, vectors (e.g. non-episomal mammalian vectors) can be integrated into the genome of a host cell upon introduction into a host cell, and thereby are replicated along with the host gene. Moreover, certain vectors are capable of directing the expression of genes to which they are operably linked. Such vectors are referred to herein as "recombinant expression vectors" (or simply, "expression vectors").

The expression vectors include plasmids, retroviruses, adenoviruses, adeno-associated viruses (AAV), plant viruses, such as cauliflower mosaic virus, tobacco mosaic virus, cosmids, YACs, EBV derived episomes, and the like. DNA molecules may be ligated into the vector such that transcriptional and translational control sequences within the vector serve their intended function of regulating the transcription and translation of the DNA. The expression vector and expression control sequences may be selected to be compatible with the expression host cell used. DNA molecules may be introduced into the expression vector by standard methods (e.g. ligation of complementary restriction sites, or blunt end ligation if no restriction sites are present).

The recombinant expression vector may also encode a leader peptide (or a signal peptide) that facilitates the secretion of the protein of interest from a host cell. The gene of the protein of interest may be cloned into the vector such that the signal peptide is linked in-frame to the amino terminus of the protein of interest. The leader peptide (or signal peptide) may be an immunoglobulin leader peptide or a heterologous leader peptide (that is, a non-immunoglobulin protein leader peptide).

In addition to the RBD-S gene of SARS-CoV-2 according to the present invention, the recombinant expression of the vectors according to the present invention may carry regulatory sequences that control the expression of the RBD-S gene of SARS-CoV-2 in a host cell. It will be understood by those skilled in the art that the design of an expression vector, including the selection of regulatory sequences, may depend on such factors as the choice of a host cell to be transformed, the level of expression of a desired protein, and so forth. Preferred control sequences for an expression host cell in mammals include viral elements that ensure high levels of protein expression in mammalian cells, such as promoters and/or enhancers derived from a retroviral LTR, cytomegalovirus (CMV) (such as a CMV promoter/enhancer), simian virus 40 (SV40) (such as a SV40 promoter/enhancer), adenovirus, (e.g. the major late promoter adenovirus (AdMLP)), polyomavirus and strong mammalian promoters such as native immunoglobulin promoter or actin promoter.

The term "control sequences" refers to DNA sequences necessary for the expression of an operably linked coding sequence in a particular host organism. The control sequences that are suitable for prokaryotes, for example, include a promoter, optionally an operator sequence and a ribosome binding site. Eukaryotic cells are known to utilize promoters, polyadenylation signals, and enhancers.

As used in the present description, the term "promoter" or "transcription regulatory sequence" or "regulatory sequence" refers to a nucleic acid fragment that controls the transcription of one or more coding sequences, and that is located upstream with respect to the direction of reading relative to the direction of transcription from the transcription initiation site of the coding sequence, and is structurally identified by the presence of a binding site for DNA-dependent RNA polymerase, transcription initiation sites and any other DNA sequences, including, but not limited to, transcription factor binding sites, repressor and activator protein binding sites, and any other sequences of nucleotides known to one of skill in the art that directly or indirectly regulate the level of transcription with said promoter. A "constitutive" promoter is a promoter that is active in most tissues under typical physiological and developmental conditions. An "inducible" promoter is a promoter that is physiologically or developmentally regulated, e.g. under the influence of a chemical inducer. A "tissue specific" promoter is only active in specific types of tissues or cells.

The terms "enhancers" or "enhancer" as used herein may refer to a DNA sequence that is located adjacent to the DNA sequence that encodes a recombinant product. Enhancer elements are typically located in a 5' direction from a promoter element or can be located downstream of or within a coding DNA sequence (e.g. a DNA sequence transcribed or translated into a recombinant product or products). Hence, an enhancer element can be located 100 base pairs, 200 base pairs, or 300 or more base pairs upstream of a DNA sequence that encodes a recombinant product, or downstream of said sequence. Enhancer elements may increase the amount of a recombinant product being expressed from a DNA sequence above the level of expression associated with a single promoter element. Multiple enhancer elements are readily available to those of ordinary skill in the art.

In addition to the above genes and regulatory sequences, recombinant expression vectors of the invention may carry additional sequences, such as sequences that regulate replication of a vector in host cells (e.g. origins of replication) and selectable marker genes. The selectable marker gene facilitates the selection of host cells into which a vector has been introduced (see e.g. U.S. Pat. Nos. 4,399,216, 4,634,665 and 5,179,017). For example, the selectable marker gene typically confers resistance to medicinal agents, such as G418, hygromycin or methotrexate, on a host cell into which the vector has been introduced. For example, selectable marker genes include a dihydrofolate reductase (DHFR) gene (for use in dhfr-host cells during methotrexate selection/amplification), a neo gene (for G418 selection), and a glutamate synthetase gene.

The term "expression control sequence" as used in the present description refers to polynucleotide sequences that are necessary to effect the expression and processing of coding sequences to which they are ligated. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (i.e., Kozak consensus sequence); sequences that enhance protein stability; and when desired, sequences that enhance protein secretion. The nature of such control sequences differs depending upon the host organism; in prokaryotes, such control sequences generally include the promoter of ribosome binding site, and transcription termination sequences; in eukaryotes, typically, such control sequences include promoters and transcription termination sequences. The term "control sequences" is intended to include at least all components, the presence of which is essential for expression and processing, and can also include additional components, the presence of which is advantageous, for example, leader sequences and fusion partner sequences.

As used herein, the term "operably linked" refers to a linkage of polynucleotide (or polypeptide) elements in a functional relationship. A nucleic acid is "operably linked" when it is present in functional relationship conditions with another nucleic acid sequence. For example, a transcription regulatory sequence is operably linked to a coding sequence if it affects the transcription of said coding sequence. The term "operably linked" means that the DNA sequences being linked are typically contiguous and, where it is necessary to join two protein coding regions, are also contiguous and are present in the reading frame.

In one embodiment of the present invention, "expression vector" relates to a vector comprising one or more polynucleotide sequences of interest, genes of interest, or "transgenes" that are flanked by parvoviral sequences or inverted terminal repeat (ITR) sequences.

Neither the cassette nor the vector of the invention comprises nucleotide sequences of genes encoding non-structural proteins (Rep) and structural proteins (Cap) of the adeno-associated virus.

AAV5 (Adeno-Associated Virus Serotype 5)-Based Recombinant Virus

In one aspect, the present invention relates to an isolated recombinant AAV5 (adeno-associated virus serotype 5)-based virus for the induction of specific immunity to SARS-CoV-2 and/or prevention of the SARS-CoV-2-associated coronavirus infection, which comprises a capsid and any of said expression cassettes.

The term "AAV-based recombinant virus" (or "AAV-based virus-like particle", or "AAV recombinant virus strain", or "AAV recombinant vector", or "rAAV vector") as used in this description refers to the above expression cassette (or the above expression vector), which is enclosed within the AAV capsid.

The Cap gene, among other alternative products, encodes 3 capsid proteins (VP1, VP2, and VP3). VP1, VP2, and VP3 are present at 1:1:10 ratio to form an icosahedral capsid (Xie Q. et al. The atomic structure of adeno-associated virus (AAV-2), a vector for human gene therapy. Proc Natl Acad Sci USA, 2002; 99:10405-10410). Transcription of these genes starts from one promoter, p40. The molecular weights of the corresponding proteins (VP1, VP2 и VP3) are 87, 72, and 62 kDa, respectively. All of the three proteins are translated from a single mRNA. Following transcription, pre-mRNA may be spliced in two different manners, where either longer or shorter intron is excised to form mRNAs of various nucleotide lengths.

During the production of the AAV (rAAV)-based recombinant virus, an expression cassette flanked by ITR is packaged into an AAV capsid. The genes required for AAV replication, as mentioned above, are not included in the cassette.

The expression cassette DNA is packaged into a viral capsid in the form of a single stranded DNA molecule (ssDNA) being approximately 3000 nucleotides long. Once a cell is infected with the virus, the single-stranded DNA is converted to the form of double-stranded DNA (dsDNA). The dsDNA can only be used by the cell's proteins, which transcribe the present gene or genes into RNA.

In some embodiments, the AAV5-based recombinant virus has a capsid that includes the AAV5 protein VP1.

In some embodiments, the AAV5-based recombinant virus has a capsid that includes the AAV5 protein VP1 having the amino acid sequence (SEQ ID NO: 4)

```
MSFVDHPPDWLEEVGEGLREFLGLEAGPPKPKPNQQHQDQARGLVLPG
YNYLGPGNGLDRGEPVNRADEVAREHDISYNEQLEAGDNPYLKYNHAD
AEFQEKLADDTSFGGNLGKAVFQAKKRVLEPFGLVEEGAKTAPTGKRI
DDHFPKRKKARTEEDSKPSTSSDAEAGPSGSQQLQIPAQPASSLGADT
MSAGGGGPLGDNNQGADGVGNASGDWHCDSTWMGDRVVTKSTRTWVLP
SYNNHQYREIKSGSVDGSNANAYFGYSTPWGYFDFNRFHSHWSPRDWQ
RLINNYWGFRPRSLRVKIFNIQVKEVTVQDSTTTIANNLTSTVQVFTD
DDYQLPYVVGNGTEGCLPAFPPQVFTLPQYGYATLNRDNTENPTERSS
```

-continued

```
FFCLEYFPSKMLRTGNNFEFTYNFEEVPFHSSFAPSQNLFKLANPLVD
QYLYRFVSTNNTGGVQFNKNLAGRYANTYKNWFPGPMGRTQGWNLGSG
VNRASVSAFATTNRMELEGASYQVPPQPNGMTNNLQGSNTYALENTMI
FNSQPANPGTTATYLEGNMLITSESETQPVNRVAYNVGGQMATNNQSS
TTAPATGTYNLQEIVPGSVWMERDVYLQGPIWAKIPETGAHFHPSPAM
GGFGLKHPPPMMLIKNTPVPGNITSFSDVPVSSFITQYSTGQVTVEME
WELKKENSKRWNPEIQYTNNYNDPQFVDFAPDSTGEYRTTRPIGTRYL
TRPL.
```

In some embodiments, the AAV5-based recombinant virus has a capsid that includes the AAV5 protein VP2.

In some embodiments, the AAV5-based recombinant virus has a capsid that includes the AAV5 protein VP2 having the following amino acid sequence:

(SEQ ID NO: 14)

```
TAPTGKRIDDHFPKRKKARTEEDSKPSTSSDAEAGPSGSQQLQIPAQP
ASSLGADTMSAGGGGPLGDNNQGADGVGNASGDWHCDSTWMGDRVVTK
STRTWVLPSYNNHQYREIKSGSVDGSNANAYFGYSTPWGYFDFNRFHS
HWSPRDWQRLINNYWGFRPRSLRVKIFNIQVKEVTVQDSTTTIANNLT
STVQVFTDDDYQLPYVVGNGTEGCLPAFPPQVFTLPQYGYATLNRDNT
ENPTERSSFFCLEYFPSKMLRTGNNFEFTYNFEEVPFHSSFAPSQNLF
KLANPLVDQYLYRFVSTNNTGGVQFNKNLAGRYANTYKNWFPGPMGRT
QGWNLGSGVNRASVSAFATTNRMELEGASYQVPPQPNGMTNNLQGSNT
YALENTMIFNSQPANPGTTATYLEGNMLITSESETQPVNRVAYNVGGQ
MATNNQSSTTAPATGTYNLQEIVPGSVWMERDVYLQGPIWAKIPETGA
HFHPSPAMGGFGLKHPPPMMLIKNTPVPGNITSFSDVPVSSFITQYST
GQVTVEMEWELKKENSKRWNPEIQYTNNYNDPQFVDFAPDSTGEYRTT
RPIGTRYLTRPL.
```

In some embodiments, the AAV5-based recombinant virus has a capsid that includes the AAV5 protein VP3.

In some embodiments, the AAV5-based recombinant virus has a capsid that includes the AAV5 protein VP3 having the following amino acid sequence (SEQ ID NO: 15)

```
MSAGGGGPLGDNNQGADGVGNASGDWHCDSTWMGDRVVTKSTRTWVLP
SYNNHQYREIKSGSVDGSNANAYFGYSTPWGYFDFNRFHSHWSPRDWQ
RLINNYWGFRPRSLRVKIFNIQVKEVTVQDSTTTIANNLTSTVQVFTD
DDYQLPYVVGNGTEGCLPAFPPQVFTLPQYGYATLNRDNTENPTERSS
FFCLEYFPSKMLRTGNNFEFTYNFEEVPFHSSFAPSQNLFKLANPLVD
QYLYRFVSTNNTGGVQFNKNLAGRYANTYKNWFPGPMGRTQGWNLGSG
VNRASVSAFATTNRMELEGASYQVPPQPNGMTNNLQGSNTYALENTMI
FNSQPANPGTTATYLEGNMLITSESETQPVNRVAYNVGGQMATNNQSS
TTAPATGTYNLQEIVPGSVWMERDVYLQGPIWAKIPETGAHFHPSPAM
```

-continued

```
GGFGLKHPPPMMLIKNTPVPGNITSFSDVPVSSFITQYSTGQVTVEME

WELKKENSKRWNPEIQYTNNYNDPQFVDFAPDSTGEYRTTRPIGTRYL

TRPL.
```

In some embodiments, the AAV5-based recombinant virus has a capsid that includes the AAV5 proteins VP1, VP2, and VP3.

In some embodiments, the AAV5-based recombinant virus has a capsid that includes the proteins VP1 with the amino acid sequence of SEQ ID NO: 4, VP2 with the amino acid sequence of SEQ ID NO: 14, and VP3 with the amino acid sequence of SEQ ID NO: 15.

In some embodiments, the AAV5-based recombinant virus has a capsid that includes the AAV5 protein VP1 having the amino acid sequence of SEQ ID NO: 4 with one or more point mutations.

In some embodiments, the AAV5-based recombinant virus has a capsid that includes an AAV5 protein VP1 having an amino acid sequence that includes amino acid substitutions at positions S2A and T711S of wild-type AAV5 VP1 (SEQ ID NO: 4), and has the amino acid sequence

```
                                              (SEQ ID NO: 5)
MAFVDHPPDWLEEVGEGLREFLGLEAGPPKPKPNQQHQDQARGLVLPGY

NYLGPGNGLDRGEPVNRADEVAREHDISYNEQLEAGDNPYLKYNHADAE

FQEKLADDTSFGGNLGKAVFQAKKRVLEPFGLVEEGAKTAPTGKRIDDH

FPKRKKARTEEDSKPSTSSDAEAGPSGSQQLQIPAQPASSLGADTMSAG

GGGPLGDNNQGADGVGNASGDWHCDSTWMGDRVVTKSTRTWVLPSYNNH

QYREIKSGSVDGSNANAYFGYSTPWGYFDFNRFHSHWSPRDWQRLINNY

WGFRPRSLRVKIFNIQVKEVTVQDSTTTIANNLTSTVQVFTDDDYQLPY

VVGNGTEGCLPAFPPQVFTLPQYGYATLNRDNTENPTERSSFFCLEYFP

SKMLRTGNNFEFTYNFEEVPFHSSFAPSQNLFKLANPLVDQYLYRFVST

NNTGGVQFNKNLAGRYANTYKNWFPGPMGRTQGWNLGSGVNRASVSAFA

TTNRMELEGASYQVPPQPNGMTNNLQGSNTYALENTMIFNSQPANPGTT

ATYLEGNMLITSESETQPVNRVAYNVGGQMATNNQSSTTAPATGTYNLQ

EIVPGSVWMERDVYLQGPIWAKIPETGAHFHPSPAMGGFGLKHPPPMML

IKNTPVPGNITSFSDVPVSSFITQYSTGQVTVEMEWELKKENSKRWNPE

IQYTNNYNDPQFVDFAPDSTGEYRSTRPIGTRYLTRPL.
```

In some embodiments, the AAV5-based recombinant virus has a capsid that includes the AAV5 protein VP2 having the amino acid sequence of SEQ ID NO: 14 with one or more point mutations.

In some embodiments, the AAV5-based recombinant virus has a capsid that includes an AAV5 protein VP2 having an amino acid sequence that includes amino acid substitutions at position T575S of wild-type AAV5 VP2 (SEQ ID NO: 14), and has the amino acid sequence

```
                                              (SEQ ID NO: 16)
TAPTGKRIDDHFPKRKKARTEEDSKPSTSSDAEAGPSGSQQLQIPAQPA

SSLGADTMSAGGGGPLGDNNQGADGVGNASGDWHCDSTWMGDRVVTKST

RTWVLPSYNNHQYREIKSGSVDGSNANAYFGYSTPWGYFDFNRFHSHWS
```

-continued

```
PRDWQRLINNYWGFRPRSLRVKIFNIQVKEVTVQDSTTTIANNLTSTVQ

VFTDDDYQLPYVVGNGTEGCLPAFPPQVFTLPQYGYATLNRDNTENPTE

RSSFFCLEYFPSKMLRTGNNFEFTYNFEEVPFHSSFAPSQNLFKLANPL

VDQYLYRFVSTNNTGGVQFNKNLAGRYANTYKNWFPGPMGRTQGWNLGS

GVNRASVSAFATTNRMELEGASYQVPPQPNGMTNNLQGSNTYALENTMI

FNSQPANPGTTATYLEGNMLITSESETQPVNRVAYNVGGQMATNNQSST

TAPATGTYNLQEIVPGSVWMERDVYLQGPIWAKIPETGAHFHPSPAMGG

FGLKHPPPMMLIKNTPVPGNITSFSDVPVSSFITQYSTGQVTVEMEWEL

KKENSKRWNPEIQYTNNYNDPQFVDFAPDSTGEYRSTRPIGTRYLTRP

L.
```

In some embodiments, the AAV5-based recombinant virus has a capsid that includes the AAV5 protein VP3 having the amino acid sequence of SEQ ID NO: 15 with one or more point mutations.

In some embodiments, the AAV5-based recombinant virus has a capsid that includes an AAV5 protein VP3 having an amino acid sequence that includes amino acid substitutions at position T519S of wild-type AAV5 VP3 (SEQ ID NO: 15), and has the amino acid sequence

```
                                              (SEQ ID NO: 17)
MSAGGGGPLGDNNQGADGVGNASGDWHCDSTWMGDRVVTKSTRTWVLPS

YNNHQYREIKSGSVDGSNANAYFGYSTPWGYFDFNRFHSHWSPRDWQRL

INNYWGFRPRSLRVKIFNIQVKEVTVQDSTTTIANNLTSTVQVFTDDDY

QLPYVVGNGTEGCLPAFPPQVFTLPQYGYATLNRDNTENPTERSSFFCL

EYFPSKMLRTGNNFEFTYNFEEVPFHSSFAPSQNLFKLANPLVDQYLYR

FVSTNNTGGVQFNKNLAGRYANTYKNWFPGPMGRTQGWNLGSGVNRASV

SAFATTNRMELEGASYQVPPQPNGMTNNLQGSNTYALENTMIFNSQPAN

PGTTATYLEGNMLITSESETQPVNRVAYNVGGQMATNNQSSTTAPATGT

YNLQEIVPGSVWMERDVYLQGPIWAKIPETGAHFHPSPAMGGFGLKHPP

PMMLIKNTPVPGNITSFSDVPVSSFITQYSTGQVTVEMEWELKKENSKR

WNPEIQYTNNYNDPQFVDFAPDSTGEYRSTRPIGTRYLTRPL.
```

In some embodiments, the AAV5-based recombinant virus has a capsid that includes the proteins VP1 with the amino acid sequence of SEQ ID NO: 4 with one or more point mutations, VP2 with the amino acid sequence of SEQ ID NO: 14 with one or more point mutations, and VP3 with the amino acid sequence of SEQ ID NO: 15 with one or more point mutations.

In some embodiments, the AAV5-based recombinant virus has a capsid that includes the proteins VP1 with the amino acid sequence of SEQ ID NO: 5, VP2 with the amino acid sequence of SEQ ID NO: 16, and VP3 with the amino acid sequence of SEQ ID NO: 17.

The phrase "more point mutations" refers to two, three, four, five, six, seven, eight, nine, or ten point substitutions.

Particularly preferred embodiments include substitutions (mutations) that are conservative in nature, i.e. substitutions that take place within a family of amino acids that are joined in their side chains. In particular, amino acids are typically divided into four families: (1) acidic amino acids are aspartate and glutamate; (2) basic amino acids are lysine, arginine, histidine; (3) non-polar amino acids are alanine, valine, leucine, isoleucine, proline, phenylalanine, methionine, tryptophan, and (4) uncharged polar amino acids are glycine, asparagine, glutamine, cysteine, serine, threonine, tyrosine. Phenylalanine, tryptophan, and tyrosine are sometimes classified as aromatic amino acids. For example, it is reasonably predictable that an isolated substitution of leucine for isoleucine or valine, an aspartate for a glutamate, a threonine for a serine, or a similar conservative substitution of an amino acid for a structurally related amino acid, will not have a major effect on the biological activity. For example, the polypeptide of interest may include up to about 5-10 conservative or non-conservative amino acid substitutions, so long as the desired function of the molecule remains intact.

An embodiment with point mutations in the sequences of AAV5 proteins VP1, VP2, or VP3 using amino acid substitutions is a substitution of at least one amino acid residue in the AAV5 protein VP1, VP2, or VP3 with another amino acid residue.

Conservative substitutions are shown in Table A under "preferred substitutions".

TABLE A

| Original residue | Exemplary substitutions | Preferred substitutions |
|---|---|---|
| Ala (A) | Val; Leu; Ile | Val |
| Arg(R) | Lys; Gin; Asn | Lys |
| Asn(N) | Gin; His; Asp, Lys; Arg | Gin |
| Asp (D) | Glu; Asn | Glu |
| Cys (C) | Ser; Ala | Ser |
| Gln(Q) | Asn; Glu | Asn |
| Glu (E) | Asp; Gin | Asp |
| Gly(G) | Ala | Ala |
| His (H) | Asn; Gin; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gin; Asn | Arg |
| Met (M) | Leu; Phe; Ile | Leu |
| Phe(F) | Trp; Leu; Val; Ile; Ala; Tyr | Tyr |
| Pro (P) | Ala | Ala |
| Ser(S) | Thr | Thr |
| Thr (T) | Val; Ser | Ser |
| Trp(W) | Tyr; Phe | Tyr |
| Tyr(Y) | Trp; Phe; Thr; Ser | Phe |
| Val (V) | Ile; Leu; Met; Phe; Ala; Norleucine | Leu |

In some embodiments, the AAV5-based recombinant virus has a capsid that includes the AAV5 protein VP1 having the amino acid sequence of SEQ ID NO: 4 or the amino acid sequence of SEQ ID NO: 4 with one or more point mutations, and the expression cassette includes the following elements in the 5'-end to 3'-end direction:

a left-hand (first) ITR (inverted terminal repeats);
a CMV (cytomegalovirus) enhancer;
a CMV (cytomegalovirus) promoter;
an intron of the hBG1 gene (hemoglobin subunit gamma 1 gene);
any one of said nucleic acids that encodes said isolated recombinant receptor-binding domain of the S glycoprotein (RBD-S) of SARS-CoV-2.
an hGH1 polyadenylation signal (human growth hormone gene polyadenylation signal);
a right-hand (second) ITR.

In some embodiments, the AAV5-based recombinant virus has a capsid that includes the proteins VP1 with the amino acid sequence of SEQ ID NO: 4, VP2 with the amino acid sequence of SEQ ID NO: 14, and VP3 with the amino acid sequence of SEQ ID NO: 15, and the expression cassette includes the following elements in the 5'-end to 3'-end direction:

a CMV enhancer;
a CMV promoter;
an intron of the hBG1 gene (hemoglobin subunit gamma 1 gene);
any one of said nucleic acids that encodes said isolated recombinant receptor-binding domain of the S glycoprotein (RBD-S) of SARS-CoV-2.
an hGH1 polyadenylation signal;
a right-hand ITR.

In some embodiments, the AAV5-based recombinant virus has a capsid that includes the proteins VP1 with the amino acid sequence of SEQ ID NO: 4 with one or more point mutations, VP2 with the amino acid sequence of SEQ ID NO: 14 with one or more point mutations, and VP3 with the amino acid sequence of SEQ ID NO: 15 with one or more point mutations, and the expression cassette includes the following elements in the 5'-end to 3'-end direction:

a CMV enhancer;
a CMV promoter;
an intron of the hBG1 gene;
any one of said nucleic acids that encodes said isolated recombinant receptor-binding domain of the S glycoprotein (RBD-S) of SARS-CoV-2.
an hGH1 polyadenylation signal;
a right-hand ITR.

In some embodiments, the AAV5-based recombinant virus has a capsid that includes the proteins VP1 with the amino acid sequence of SEQ ID NO: 5, VP2 with the amino acid sequence of SEQ ID NO: 16, and VP3 with the amino acid sequence of SEQ ID NO: 17, and the expression cassette includes the following elements in the 5'-end to 3'-end direction:

a CMV enhancer;
a CMV promoter;
an intron of the hBG1 gene;
any one of said nucleic acids that encodes said isolated recombinant receptor-binding domain of the S glycoprotein (RBD-S) of SARS-CoV-2.
an hGH1 polyadenylation signal;
a right-hand ITR.

In some embodiments, the AAV5-based recombinant virus has a capsid that includes the AAV5 protein VP1 having the amino acid sequence of SEQ ID NO: 4 or the amino acid sequence of SEQ ID NO: 4 with one or more point mutations, and the expression cassette comprises a nucleic acid with SEQ ID NO: 3.

In some embodiments, the AAV5-based recombinant virus has a capsid that includes the AAV5 protein VP1 having the amino acid sequence of SEQ ID NO: 4 with one or more point mutations, the AAV5 protein VP1 is the amino acid sequence of SEQ ID NO: 5 (S2A and T711S).

In some embodiments, the AAV5-based recombinant virus has a capsid that includes the proteins VP1 with the amino acid sequence of SEQ ID NO: 4, VP2 with the amino acid sequence of SEQ ID NO: 14, and VP3 with the amino acid sequence of SEQ ID NO: 15, and the expression cassette comprises a nucleic acid with SEQ ID NO: 3.

In some embodiments, the AAV5-based recombinant virus has a capsid that includes the proteins VP1 with the amino acid sequence of SEQ ID NO: 4 with one or more point mutations, VP2 with the amino acid sequence of SEQ ID NO: 14 with one or more point mutations, and VP3 with the amino acid sequence of SEQ ID NO: 15 with one or more point mutations, and the expression cassette comprises a nucleic acid with SEQ ID NO: 3.

In some embodiments, the AAV5-based recombinant virus has a capsid that includes the proteins VP1 with the amino acid sequence of SEQ ID NO: 5, VP2 with the amino acid sequence of SEQ ID NO: 16, and VP3 with the amino acid sequence of SEQ ID NO: 17, and the expression cassette comprises a nucleic acid with SEQ ID NO: 3.

Pharmaceutical Composition/Vaccine

In one aspect, the present invention relates to a pharmaceutical composition for the prevention of SARS-CoV-2-associated coronavirus infection, which comprises any of said recombinant AAV5-based viruses in combination with one or more pharmaceutically acceptable excipients.

In one aspect, the present invention relates to a pharmaceutical composition for the induction of specific immunity to SARS-CoV-2, which comprises any of said recombinant AAV5-based viruses in combination with one or more pharmaceutically acceptable excipients.

In particular embodiments, the present invention relates to a pharmaceutical composition comprising the AAV5-based recombinant virus of the invention in a pharmaceutically acceptable carrier or in other pharmaceutical agents, adjuvants, diluents, etc. For injection, the carrier will typically be a liquid carrier. For other methods of administration, the carrier may be either solid or liquid, such as sterile pyrogen-free water or sterile pyrogen-free phosphate-buffered saline solution. For inhalation administration, the carrier is respirable, and preferably is in a solid or liquid particulate form. As an injection medium, it is preferred to use water that contains the additives that are common for injection solutions, such as stabilizing agents, salts or saline, and/or buffers.

"Pharmaceutical composition" means a composition comprising the above AAV5-based recombinant virus of the invention and at least one of components selected from the group consisting of pharmaceutically acceptable and pharmacologically compatible excipients, such as fillers, solvents, diluents, carriers, auxiliary, distributing agents, delivery agents, preservatives, stabilizers, emulsifiers, suspending agents, thickeners, prolonged delivery controllers, the choice and proportions of which depend on the type and route of administration and dosage. Pharmaceutical compositions of the present invention and methods for preparation thereof will be undoubtedly apparent to those skilled in the art. Pharmaceutical compositions should preferably be manufactured in compliance with the GMP (Good Manufacturing Practice) requirements. A composition may comprise a buffer composition, tonicity agents, stabilizers and solubilizers.

"Pharmaceutically acceptable" means a material that does not have biological or other negative side effects, for example, the material can be administered to a subject without causing any undesirable biological effects. Thus, such pharmaceutical compositions may be used, for example, in transfection of a cell ex vivo or in administration in vivo of the AAV5-based recombinant virus of the invention directly to a subject.

The term "excipient" is used herein to describe any ingredient other than the above ingredients of the invention. These are substances of inorganic or organic nature which are used in the pharmaceutical manufacturing in order to give drug products the necessary physicochemical properties.

"Stabilizer" refers to an excipient or a mixture of two or more excipients that provide the physical and/or chemical stability of the active agent.

The term "buffer", "buffer composition", "buffering agent" refers to a solution, which is capable of resisting changes in pH by the action of its acid-base conjugate components, which allows the rAAV5 vector product to resist changes in pH. Generally, the pharmaceutical composition preferably has a pH in the range from 4.0 to 8.0. Examples of buffers that can be used include, but are not limited to, acetate, phosphate, citrate, histidine, succinate, etc. buffer solutions.

A pharmaceutical composition is "stable" if the active agent retains physical stability and/or chemical stability and/or biological activity thereof during the specified shelf life at storage temperature, for example, of 2-8° C. Preferably, the active agent retains both physical and chemical stability, as well as biological activity. Storage period is adjusted based on the results of stability test in accelerated or natural aging conditions.

A pharmaceutical composition of the invention can be manufactured, packaged, or widely sold in the form of a single unit dose or a plurality of single unit doses in the form of a ready formulation. The term "single unit dose" as used herein refers to a discrete quantity of a pharmaceutical composition containing a predetermined quantity of an active ingredient. The quantity of the active ingredient typically equals the dose of the active ingredient to be administered in a subject, or a convenient portion of such dose, for example, half or a third of such dose.

In one aspect, the present invention relates to a vaccine for the prevention of SARS-CoV-2-associated coronavirus infection, which comprises any of said recombinant AAV5-based viruses in an effective amount.

In one aspect, the present invention relates to a vaccine for the induction of specific immunity to SARS-CoV-2, which comprises any of said recombinant AAV5-based viruses in an effective amount.

The term "vaccine" refers to an immunogenic composition comprising an antigen derived from a pathogen that is used to induce an immune response against a pathogen that confers protective immunity (e.g., immunity that protects a subject from an infection caused by a pathogen and/or reduces the severity of a disease or a condition caused by an infection as a result of a pathogen). Protective immunity may include the production of antibodies and/or cell-mediated response.

Depending on the context, the term "vaccine" may also refer to an antigen suspension or solution that is administered to a vertebrate to develop protective immunity.

The vaccine includes an AAV5-based recombinant virus, which is present therein preferably in a biologically effective amount. A "biologically effective" amount of the recombinant virus is an amount that is sufficient to cause infection (or transduction) and expression of the heterologous nucleic acid sequence in the cell. If the virus is administered to a cell in vivo (e.g. the virus is administered to a subject, as described below), a "biologically-effective" amount of the viral vector is an amount that is sufficient to cause the transduction and expression of the heterologous nucleic acid sequence in the target cell.

All definitions and explanations relating to the pharmaceutical composition shall also apply to the vaccine.

Use

In one aspect, the present invention relates to the use of any of said recombinant AAV5-based viruses or said pharmaceutical composition for the prevention of SARS-CoV-2-associated coronavirus infection.

In one aspect, the present invention relates to the use of any of said recombinant AAV5-based viruses or said pharmaceutical composition for the induction of specific immunity to SARS-CoV-2.

In one aspect, the present invention relates to a method for the induction of specific immunity to SARS-CoV-2, which comprises administering to a mammalian organism any one of said recombinant AAV5-based viruses, said composition or said vaccine for the induction of specific immunity to SARS-CoV-2, in an effective amount.

In one aspect, the present invention relates to a method for preventing SARS-CoV-2-associated coronavirus infection, which comprises administering to a mammalian organism any one of said recombinant AAV5-based viruses, said composition or said vaccine for the prevention of SARS-CoV-2-associated coronavirus infection, in an effective amount.

Any method for administering the AAV5-based recombinant virus, which is recognized in the art, can be suitably used for the above AAV5-based recombinant virus of the present invention.

Exemplary modes of administration include topical application, intranasal, inhalation, transmucosal, transdermal, enteral (e.g. oral, rectal), parenteral (e.g. intravenous, subcutaneous, intradermal, intramuscular) administrations, as well as direct tissue or organ injections.

Injectables can be prepared in conventional forms, either as liquid solutions or suspensions, solid forms suitable for the preparation of solution or suspensions in liquid prior to injection, or as emulsions. Alternatively, one may administer said AAV5-based recombinant virus of the present invention in a local rather than systemic manner, for example in a depot or sustained-release formulation.

The AAV5-based recombinant virus is introduced into an organism in an effective amount. The AAV5-based recombinant virus is preferably introduced into an organism in a biologically effective amount. A "biologically effective" amount of the recombinant virus is an amount that is sufficient to cause infection (or transduction) and expression of the heterologous nucleic acid sequence in the cell. If the virus is administered to a cell in vivo (e.g. the virus is administered to a subject, as described below), a "biologically-effective" amount of the viral vector is an amount that is sufficient to cause the transduction and expression of the heterologous nucleic acid sequence in the target cell.

Dosages of said AAV5-based recombinant virus of the invention will depend on the mode of administration, the particular viral vector, and they can be determined in a routine manner. Exemplary doses for achieving therapeutic effects are viral titers of at least about $10^5$, $10^6$, $10^7$, $10^8$, $10^9$, $10^{10}$, $10^{11}$, $10^{12}$, $10^{13}$, $10^{14}$, $10^{15}$, $10^{16}$ transducting units or more, preferably about $10^8$ to $10^{13}$ transducting units, yet more preferably $10^{12}$ transducing units.

The cell for administering said AAV5-based recombinant virus of the invention may be a cell of any type, including but not limited to epithelial cells (e.g. skin, respiratory and gut epithelial cells), hepatic cells, muscle cells, pancreatic cells (including islet cells), hepatic cells, spleen cells, fibroblasts, endothelial cells, and the like.

The above AAV5-based recombinant virus is not used to modify the genetic integrity of human germ line cells.

EXAMPLES

The following examples are provided for a better understanding of the invention. These examples are for purposes of illustration only and are not to be construed as limiting the scope of the invention in any manner.

All publications, patents, and patent applications cited in this specification are incorporated herein by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended embodiments.

Materials and General Methods

Recombinant DNA Techniques

DNA manipulations were carried out by standard techniques as described by Sambrook J. et al, Molecular cloning: A laboratory manual; Cold Spring Harbor Laboratory Press, Cold Spring Harbor, New York, 1989. Molecular biological reagents were used according to the manufacturer instructions. Briefly, plasmid DNA was produced for further manipulation in *E. coli* cells grown under selective antibiotic pressure so that the plasmids were not lost in the cell population. We isolated the plasmid DNA from cells using commercial kits, measured the concentration, and used it for cloning by restriction endonuclease treatment or PCR amplification. The DNA fragments were ligated to each other using ligases and transformed into bacterial cells for the selection of clones and further production. All resulting genetic constructs were confirmed by restriction patterns and complete Sanger sequencing.

Gene Synthesis

Desired gene segments were prepared from oligonucleotides made by chemical synthesis. Gene segments of 300 to 1000 bp long, which were flanked by unique restriction sites, were collected by renaturing oligonucleotides on top of each other, followed by PCR amplification from border primers. As a result, a mixture of fragments was produced, including the desired one. The fragments were cloned at restriction sites into intermediate vectors, following which the DNA sequences of the subcloned fragments were confirmed by DNA sequencing.

DNA Sequence Determination

DNA sequences were determined by Sanger sequencing. DNA and protein sequences were analyzed and sequence data was processed in SnapGene Viewer 4.2 or higher for sequence creation, mapping, analysis, annotation and illustration.

Culturing Cell Cultures

The experiments used HEK293 (Human Embryonic Kidney clone 293) and CHO-K1-S(Chinese Hamster Ovary Cells) cell lines. The suspended HEK293 cells used to produce AAV were cultured under standard conditions at 37° C. and 5% $CO_2$ on a complete culture medium without FBS and an antibiotic. The adherent CHO-K1-S cells used to test the efficacy of AAV products were cultured under standard conditions at 37° C. and 5% $CO_2$, on a complete DMEM/F12 medium supplemented with 5% FBS, antibiotic/antimycotic. The CHO-K1-S cells were subcultured upon reaching 80-90% confluence. Cell viability was assessed using either Trypan Blue stain and a hemocytometer or PI stain and flow cytometry.

Determination of the Levels of RBD-S Protein and Specific Antibodies to RBD-S Protein The content of RBD-S protein following transduction of cells and antibodies to RBD-S protein in the blood plasma of animals following immunization was assessed by enzyme-linked immunosorbent assay (ELISA) using horseradish peroxidase as an indicator enzyme. Briefly, the wells of a 96-well plate were sensitized with primary antibodies to RBD-S protein, followed by layering the test samples. When ELISA was employed to detect antibodies to RBD-S protein, the plate was sensitized with RBD-S protein, followed by adding the blood plasma of the animals to the wells. Next, the samples were supplemented with secondary antibodies to RBD-S (analysis for the protein itself) or secondary antibodies to immunoglobulins of the research animals (analysis for the presence of antibodies to RBD-S) labeled with biotin and HRP-conjugated streptavidin. Next, a TMB solution was added to visualize the enzymatic reaction, and a stop solution was added to stop the development of the reaction.

To determine the concentration of RBD-S/antibodies to RBD-S in the test samples, we plotted a calibration curve showing the dependence of the optical density of the solution on the concentration of RBD-S/antibodies to RBD-S in standard samples, and we used optical density to determine the concentration of the test sample.

Assembly and Purification of Viral Particles of Recombinant AAV Vectors

Figure 1:
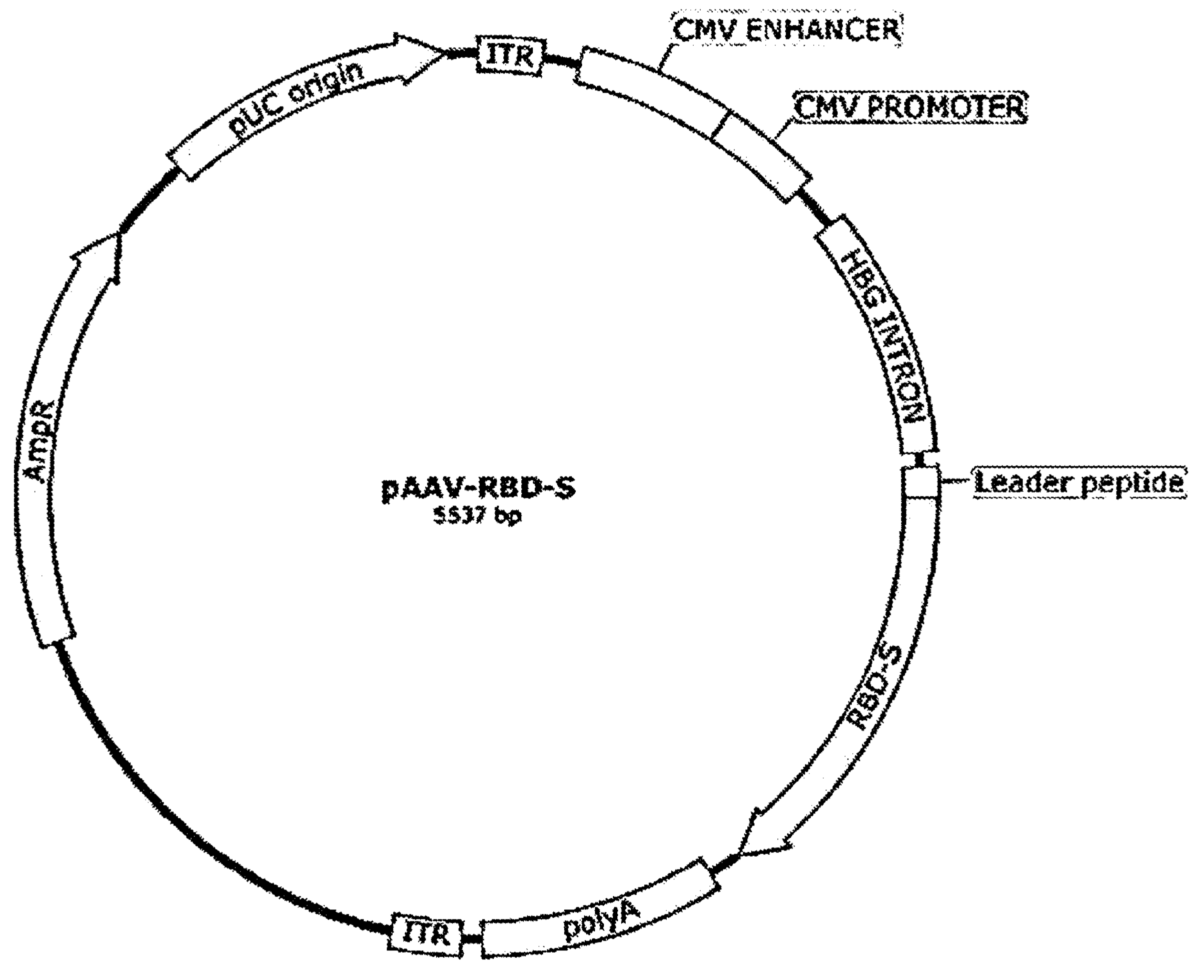
FIG. 1 is a schematic diagram of the plasmid pAAV-RBD-S intended to produce an AAV vector with an expression cassette comprising the RBD-S gene sequence of the recombinant receptor-binding domain of the S glycoprotein (RBD-S) of SARS-CoV-2

To assemble AAV particles containing the RBD-S gene, we used HEK293 producer cells, into which 3 plasmids were transfected as follows:

- pAAV-RBD-S plasmid comprising the AAV genome with RBD-S transgene expression cassette (FIG. 1);
- A plasmid for expression of the AAV5 serotype Cap gene and the AAV2 serotype Rep gene. Each gene, using alternative reading frames, encodes several protein products;
- A plasmid for expression of Ad5 (adenovirus serotype 5) genes that are required for assembly and packaging of AAV capsids.

After 72 hours, the cells were lysed and the viral particles were purified and concentrated using filtration, chromatography and ultracentrifugation methods. The titer of the viral particles was determined by quantitative PCR with primers and a sample that were specific for the region of the recombinant viral genome and expressed as the copy number of viral genomes per 1 ml.

Transduction of Cell Cultures

The cell line was pre-seeded into the wells of 6-well plates at a seeding density of 10,000 cells/cm$^2$, followed by adding the viral particle product at an MOI of 100,000 vg/cell and an MOI of 500,000 vg/cell, on day 3 the RBD-S protein content was determined by ELISA, as described above. Transduction efficiency was estimated by measuring the percentage of GFP+ cells.

Following transduction, the CHO-K1-S cells were removed from the culture plates using TrypLE and washed in PBS; protein expression was analyzed as described above.

All measurements were carried out in 3 independent experiments. Intact cells were used as a negative control.

In Vivo Study on Laboratory Animals

The experiments were performed on BALB/c mice (males and females aged 6-8 weeks). Immunization was carried out by a single intramuscular injection of the products into the pelvic limbs. The negative control group of animals was injected with a buffer solution, the positive control group was injected with a mixture of RBD-S protein, Freund's complete adjuvant and saline.

Blood plasma was collected on the day of injection before the administration of the products, then on days 14, 21, 27, 42 and 56 following immunization.

Example 1. Selection of RBD-S Sequence of SARS-CoV-2

The development of the RBD-S antigen of SARS-CoV-2 included the analysis of the 5WRG structure of the spike glycoprotein of SARS-CoV provided in ET AL., Cryo-electron microscopy structures of the SARS-CoV spike glycoprotein reveal a prerequisite conformational state for receptor binding, 2017, Cell Res. 27, p. 119-129. Our analysis of the structure of SARS-CoV spike glycoprotein showed that it was possible to use both the conserved RBD-S and its extended portion for immunization. Our analysis revealed that the increased length of RBD-S in question should contribute to the stabilization of the RBD-S protein structure due to the preservation of secondary structures that increase the likelihood of maintaining a stable protein conformation without the need to unwind. Further, a slight increase in the length of RBD-S should not affect the results of immunization. The above analysis of the structure of SARS-CoV spike glycoprotein was extrapolated to the structure of SARS-CoV-2 spike glycoprotein. Furthermore, the substitution of the unpaired cysteine, which is closest to the domain, to serine (amino acid substitution at position C272S) was introduced into the structure of the RBD-S protein of SARS-CoV-2 to provide additional stability of the RBD-S protein of SARS-CoV-2.

Thus, the following amino acid sequence with SEQ ID NO: 1 was selected as the SARS-CoV-2 RBD-S antigen.

This antigen will be used to effectively immunize mammals (see Example 5).

Example 2. Assembly of a Genetic Construct Comprising an AAV Expression Cassette with a Recombinant RBD-S Gene The target plasmid pAAV-RBD-S (FIG. 1) intended for the production of AAV5 viral vectors with an expression cassette comprising the RBD-S gene (SEQ ID NO: 1) was produced by substituting the sequence of the modified green fluorescent protein in the original construct pAAV-GFP Control plasmid (VPK-402) from CellBiolab (USA) using the restriction enzyme ligase method of cloning at ClaI/BamHI sites to the RBD-S sequence with a signal peptide, the RBD-S sequence being synthesized de novo from oligonucleotides generated by chemical synthesis, with adding ClaI restriction sites from the 5'-end and BamHI restriction sites from the 3'-end.

The final vector contains all the necessary elements for expression and assembly of the gene as part of the recombinant AAV genome:

1) ITRs at the ends of the sequence that is encapsidated into a viral capsid;
2) Elements for expression of the target gene (promoter, enhancer, intron, Kozak sequence, transgene, polyadenylation site);
3) The bacterial replication origin and antibiotic resistance gene to produce plasmid DNA in bacterial cells.

Example 3. Creation of Viral Products Expressing RBD-S

The target plasmid pAAV-RBD-S (FIG. 1) together with the rest of the plasmids required to produce recombinant AAV viral particles (see above) were used to produce the AAV5-RBD-S product. The bioprocessing resulted in recombinant AAV5-RBD-S viral particles comprising an expression cassette with the RBD-S gene. The purified AAV5-RBD-S product used for in vitro and in vivo studies was prepared using standard buffers and excipients that are safe and do not alter the AAV properties. The concentration of the purified AAV5-RBD-S product was $4.6\times10^{11}$ and $1.8\times10^{12}$ VG/mL.

Example 4. In Vitro Testing of the AAV5-RBD-S Product

The purified AAV5-RBD-S product was tested in vitro prior to animal studies. These experiments were performed using the CHO-K1-S adherent cell line (FIG. 2). The CHO-K1-S cells were plated into the wells of 6-well plates. Seeding was made into the following growth medium: DMEM/F12 supplemented with glutamine, glucose content was 4.5 g/l, 5% fetal bovine serum (FBS).

Cell seeding density was 10,000 cell/cm$^2$. During the transduction run, pre-prepared cells were transduced at MOI of 100,000 vg/cell and at MOI of 500,000 vg/cell. All samples were run in triplicates. Intact cells were used as a negative control. Following successful transduction, the CHO-K1-S cells were removed from the substrate, washed in a phosphate buffer, and the expression of the RBD-S protein was analyzed by enzyme-linked immunosorbent assay (ELISA) as described above. It has been shown that the product that we developed makes it possible to efficiently deliver the RBD-S transgene into cells and ensure the production of the target protein, which is confirmed by ELISA data (FIG. 2).

Example 5. In Vivo Testing of the AAV5-RBD-S Product

The in vivo study of the AAV5-RBD-S product used BALB/c laboratory mice. The study used two different doses of the AAV5-RBD-S product as follows: a low dose ($1\times10^{11}$ VG/mouse) and s high dose ($4\times10^{11}$ VG/mouse). A control solution without AAV and the AAV5 product without an expression cassette with the RBD-S gene (empty AAV5 capsids) were used as negative controls. A purified recombinant RBD-S protein was used as a positive control. Animals were immunized by a single intramuscular injection into the pelvic limbs. On days 0, 14, 21, 27, 42 and 56 following immunization, the titer of antibodies to the RBD-S protein in blood plasma was determined by ELISA, as described above. The in vivo studies has shown that immunization with AAV5-RBD-S products results in the production of specific antibodies to RBD-S (FIGS. 3, 4, 5 and 6). Further, the level of antibodies to RBD-S was comparable to the that in the group of animals immunized with the recombinant RBD-S protein (FIGS. 8 and 9). At the same time, the production of antibodies to RBD-S was not observed in groups of animals that were injected with a control solution without AAV and the AAV5 product that did not contain an expression cassette with the RBD-S gene (empty AAV5 capsids) (FIG. 7, 10).

Thus, the recombinant AAV5-based virus according to the invention and the vaccine based thereon have a high potential for the induction of specific immunity to SARS-CoV-2 and may be used in the prevention of SARS-CoV-2-related coronavirus infection. Furthermore, since the AAV vector is capable of providing long-term antigen expression, they are advantageous over traditional systems based on recombinant protein antigens.

The invention claimed is:

1. An isolated recombinant receptor-binding domain of the S glycoprotein (RBD-S) of SARS-CoV-2, which comprises the amino acid sequence of SEQ ID NO: 1.

2. An isolated nucleic acid that encodes the isolated recombinant receptor-binding domain of the S glycoprotein (RBD-S) of SARS-CoV-2 according to claim 1.

3. The isolated nucleic acid of claim 2, wherein the nucleic acid is DNA.

4. The isolated nucleic acid of claim 2, wherein the isolated nucleic acid is the nucleotide sequence of SEQ ID NO:2.

5. The isolated nucleic acid of claim 2, wherein the isolated nucleic acid is a codon-optimized nucleotide sequence.

6. An expression cassette comprising the nucleic acid according to claim 2.

7. The expression cassette of claim 6, comprising the following elements in the 5'-end to 3'-end direction:

a left-hand (first) ITR (inverted terminal repeats);

a CMV (cytomegalovirus) enhancer;

a CMV (cytomegalovirus) promoter;

an intron of the hBG1 gene (hemoglobin subunit gamma 1 gene);

an isolated nucleic acid that encodes an isolated recombinant receptor-binding domain of the S glycoprotein (RBD-S) of SARS-CoV-2 which comprises the amino acid sequence of SEQ ID NO:1;

an hGH1 polyadenylation signal (human growth hormone gene polyadenylation signal); and a right-hand (second) ITR.

8. The expression cassette of claim 7 that comprises the nucleic acid of SEQ ID NO: 3.

9. An expression vector comprising an isolated nucleic acid that encodes an isolated recombinant receptor-binding domain of the S glycoprotein (RBD-S) of SARS-CoV-2 which comprises the amino acid sequence of SEQ ID NO:1 or the cassette according to claim 6.

10. An isolated recombinant AAV5 (adeno-associated virus serotype 5)-based virus for the induction of specific immunity to SARS-CoV-2, which comprises a capsid and the expression cassette according to claim 6.

11. The AAV5-based recombinant virus according to claim 10, wherein the capsid comprises the AAV5 protein VP1.

12. The AAV5-based recombinant virus according to claim 11, wherein the capsid comprises the AAV protein VP1 having the amino acid sequence of SEQ ID NO: 4.

13. The AAV5-based recombinant virus according to claim 10, wherein the capsid comprises the AAV5 protein VP1 having the amino acid sequence of SEQ ID NO: 4 with one or more point mutations.

14. The AAV5-based recombinant virus according to claim 13, wherein the capsid comprises the AAV protein VP1 having the amino acid sequence of SEQ ID NO: 5.

15. The AAV5-based recombinant virus according to claim 10, wherein the capsid comprises the AAV5 protein VP1 having the amino acid sequence of SEQ ID NO: 4 or the amino acid sequence of SEQ ID NO: 4 with one or more point mutations, and the expression cassette comprises the following elements in the 5'-end to 3'-end direction:

a left-hand (first) ITR (inverted terminal repeats);

a CMV (cytomegalovirus) enhancer;

a CMV (cytomegalovirus) promoter;

an intron of the hBG1 gene (hemoglobin subunit gamma 1 gene);

an isolated nucleic acid that encodes an isolated recombinant receptor-binding domain of the S glycoprotein (RBD-S) of SARS-CoV-2 which comprises the amino acid sequence of SEQ ID NO:1;

an hGH1 polyadenylation signal (human growth hormone gene polyadenylation signal); and a right-hand (second) ITR.

16. The AAV5-based recombinant virus according to claim 15, wherein the capsid includes the AAV5 protein VP1 having the amino acid sequence of SEQ ID NO: 4 or the amino acid sequence of SEQ ID NO: 4 with one or more point mutations, and the expression cassette comprises the nucleic acid of SEQ ID NO: 3.

17. The AAV5-based recombinant virus according to claim 15, wherein the AAV5 protein VP1 having the amino acid sequence of SEQ ID NO: 4 with one or more point mutations is the amino acid sequence of SEQ ID NO: 5.

18. A pharmaceutical composition comprising the recombinant AAV5-based virus according to claim 10 in combination with one or more pharmaceutically acceptable excipients.

19. The pharmaceutical composition according to claim 18 for the induction of specific immunity to SARS-CoV-2.

20. A vaccine for the induction of specific immunity to SARS-CoV-2, which comprises the recombinant AAV5-based virus according to claim 10 in an effective amount.

21. A method for the induction of specific immunity to SARS-CoV-2, comprising administering to a mammalian organism the recombinant AAV5-based virus according to claim 10 for the induction of specific immunity to SARS-CoV-2, in an effective amount.

* * * * *

SEQUENCE LISTING

```
<160> NUMBER OF SEQ ID NOS: 17

<210> SEQ ID NO 1
<211> LENGTH: 278
<212> TYPE: PRT
<213> ORGANISM: Artificial sequence
<220> FEATURE:
<223> OTHER INFORMATION: recombinant receptor-binding domain of
      glycoprotein S (RBD-S), SARS-CoV-2

<400> SEQUENCE: 1

Arg Val Gln Pro Thr Glu Ser Ile Val Arg Phe Pro Asn Ile Thr Asn
1               5                   10                  15

Leu Cys Pro Phe Gly Glu Val Phe Asn Ala Thr Arg Phe Ala Ser Val
            20                  25                  30

Tyr Ala Trp Asn Arg Lys Arg Ile Ser Asn Cys Val Ala Asp Tyr Ser
        35                  40                  45

Val Leu Tyr Asn Ser Ala Ser Phe Ser Thr Phe Lys Cys Tyr Gly Val
    50                  55                  60

Ser Pro Thr Lys Leu Asn Asp Leu Cys Phe Thr Asn Val Tyr Ala Asp
65                  70                  75                  80

Ser Phe Val Ile Arg Gly Asp Glu Val Arg Gln Ile Ala Pro Gly Gln
                85                  90                  95

Thr Gly Lys Ile Ala Asp Tyr Asn Tyr Lys Leu Pro Asp Asp Phe Thr
            100                 105                 110

Gly Cys Val Ile Ala Trp Asn Ser Asn Asn Leu Asp Ser Lys Val Gly
        115                 120                 125

Gly Asn Tyr Asn Tyr Leu Tyr Arg Leu Phe Arg Lys Ser Asn Leu Lys
    130                 135                 140

Pro Phe Glu Arg Asp Ile Ser Thr Glu Ile Tyr Gln Ala Gly Ser Thr
145                 150                 155                 160
```

```
Pro Cys Asn Gly Val Glu Gly Phe Asn Cys Tyr Phe Pro Leu Gln Ser
                165                 170                 175

Tyr Gly Phe Gln Pro Thr Asn Gly Val Gly Tyr Gln Pro Tyr Arg Val
            180                 185                 190

Val Val Leu Ser Phe Glu Leu Leu His Ala Pro Ala Thr Val Cys Gly
        195                 200                 205

Pro Lys Lys Ser Thr Asn Leu Val Lys Asn Lys Cys Val Asn Phe Asn
    210                 215                 220

Phe Asn Gly Leu Thr Gly Thr Gly Val Leu Thr Glu Ser Asn Lys Lys
225                 230                 235                 240

Phe Leu Pro Phe Gln Gln Phe Gly Arg Asp Ile Ala Asp Thr Thr Asp
                245                 250                 255

Ala Val Arg Asp Pro Gln Thr Leu Glu Ile Leu Asp Ile Thr Pro Ser
            260                 265                 270

Ser Phe Gly Gly Val Ser
        275
```

<210> SEQ ID NO 2
<211> LENGTH: 834
<212> TYPE: DNA
<213> ORGANISM: Artificial sequence
<220> FEATURE:
<223> OTHER INFORMATION: Nucleic acid of RBD-S of SARS-CoV-2

<400> SEQUENCE: 2

```
agagtccaac caacagaatc tattgttaga tttcctaata ttacaaactt gtgccctttt     60

ggtgaagttt ttaacgccac cagatttgca tctgtttatg cttggaacag gaagagaatc    120

agcaactgtg ttgctgatta ttctgtccta tataattccg catcattttc cacttttaag    180

tgttatggag tgtctcctac taaattaaat gatctctgct ttactaatgt ctatgcagat    240

tcatttgtaa ttagaggtga tgaagtcaga caaatcgctc cagggcaaac tggaaagatt    300

gctgattata attataaatt accagatgat tttacaggct gcgttatagc ttggaattct    360

aacaatcttg attctaaggt tggtggtaat tataattacc tgtatagatt gtttaggaag    420

tctaatctca aaccttttga gagagatatt tcaactgaaa tctatcaggc cggtagcaca    480

ccttgtaatg gtgttgaagg ttttaattgt tactttcctt tacaatcata tggtttccaa    540

cccactaatg gtgttggtta ccaaccatac agagtagtag tactttcttt tgaacttcta    600

catgcaccag caactgtttg tggacctaaa aagtctacta atttggttaa aaacaaatgt    660

gtcaatttca acttcaatgg tttaacaggc acaggtgttc ttactgagtc taacaaaaag    720

tttctgcctt tccaacaatt tggcagagac attgctgaca ctactgatgc tgtccgtgat    780

ccacagacac ttgagattct tgacattaca ccatcttctt ttggtggtgt cagt          834
```

<210> SEQ ID NO 3
<211> LENGTH: 2940
<212> TYPE: DNA
<213> ORGANISM: Artificial sequence
<220> FEATURE:
<223> OTHER INFORMATION: expression cassette with gene of RBD-S of SARS-CoV-2

<400> SEQUENCE: 3

```
cctgcaggca gctgcgcgct cgctcgctca ctgaggccgc ccgggcgtcg ggcgaccttt     60

ggtcgcccgg cctcagtgag cgagcgagcg cgcagagagg gagtggccaa ctccatcact    120

aggggttcct gcggccgcac gcgtctagtt attaatagta atcaattacg gggtcattag    180
```

```
ttcatagccc atatatggag ttccgcgtta cataacttac ggtaaatggc ccgcctggct    240
gaccgcccaa cgacccccgc ccattgacgt caataatgac gtatgttccc atagtaacgc    300
caatagggac tttccattga cgtcaatggg tggagtattt acggtaaact gcccacttgg    360
cagtacatca agtgtatcat atgccaagta cgccccctat tgacgtcaat gacggtaaat    420
ggcccgcctg gcattatgcc cagtacatga ccttatggga ctttcctact tggcagtaca    480
tctacgtatt agtcatcgct attaccatgg tgatgcggtt ttggcagtac atcaatgggc    540
gtggatagcg gtttgactca cggggatttc caagtctcca ccccattgac gtcaatggga    600
gtttgttttg gcaccaaaat caacgggact ttccaaaatg tcgtaacaac tccgccccat    660
tgacgcaaat gggcggtagg cgtgtacggt gggaggtcta tataagcaga gctcgtttag    720
tgaaccgtca gatcgcctgg agacgccatc cacgctgttt tgacctccat agaagacacc    780
gggaccgatc cagcctccgc ggattcgaat cccggccggg aacggtgcat tggaacgcgg    840
attccccgtg ccaagagtga cgtaagtacc gcctatagag tctataggcc cacaaaaaat    900
gctttcttct tttaatatac tttttttgttt atcttatttc taatactttc cctaatctct    960
ttctttcagg gcaataatga tacaatgtat catgcctctt tgcaccattc taaagaataa   1020
cagtgataat ttctgggtta aggcaatagc aatatttctg catataaata tttctgcata   1080
taaattgtaa ctgatgtaag aggtttcata ttgctaatag cagctacaat ccagctacca   1140
ttctgctttt attttatggt tgggataagg ctggattatt ctgagtccaa gctaggccct   1200
tttgctaatc atgttcatac ctcttatctt cctcccacag ctcctgggca acgtgctggt   1260
ctgtgtgctg gcccatcact ttggcaaaga attgggattc gaacatcgcg ataattagcc   1320
gccaccatgg agaccgacac cctgctgctg tgggtgctgc tgctgtgggt gcccgggtcg   1380
accgggagag tccaaccaac agaatctatt gttagatttc ctaatattac aaacttgtgc   1440
ccttttggtg aagtttttaa cgccaccaga tttgcatctg tttatgcttg gaacaggaag   1500
agaatcagca actgtgttgc tgattattct gtcctatata attccgcatc attttccact   1560
tttaagtgtt atggagtgtc tcctactaaa ttaaatgatc tctgctttac taatgtctat   1620
gcagattcat ttgtaattag aggtgatgaa gtcagacaaa tcgctccagg gcaaactgga   1680
aagattgctg attataatta taaattacca gatgatttta caggctgcgt tatagcttgg   1740
aattctaaca atcttgattc taaggttggt ggtaattata attacctgta tagattgttt   1800
aggaagtcta atctcaaacc ttttgagaga gatatttcaa ctgaaatcta tcaggccggt   1860
agcacacctt gtaatggtgt tgaaggtttt aattgttact ttcctttaca atcatatggt   1920
ttccaaccca ctaatggtgt tggttaccaa ccatacagag tagtagtact ttcttttgaa   1980
cttctacatg caccagcaac tgtttgtgga cctaaaaagt ctactaattt ggttaaaaac   2040
aaatgtgtca atttcaactt caatggttta acaggcacag gtgttcttac tgagtctaac   2100
aaaaagtttc tgcctttcca acaatttggc agagacattg ctgacactac tgatgctgtc   2160
cgtgatccac agacacttga gattcttgac attacaccat cttcttttgg tggtgtcagt   2220
taaggatcct ctagagtcga cctgcagaag cttgcctcga gcagcgctgc tcgagagatc   2280
tacgggtggc atccctgtga cccctcccca gtgcctctcc tggccctgga agttgccact   2340
ccagtgccca ccagccttgt cctaataaaa ttaagttgca tcattttgtc tgactaggtg   2400
tccttctata atattatggg gtggaggggg gtggtatgga gcaaggggca agttgggaag   2460
acaacctgta gggcctgcgg ggtctattgg gaaccaagct ggagtgcagt ggcacaatct   2520
```

```
tggctcactg caatctccgc ctcctgggtt caagcgattc tcctgcctca gcctcccgag   2580

ttgttgggat tccaggcatg catgaccagg ctcagctaat ttttgttttt ttggtagaga   2640

cggggtttca ccatattggc caggctggtc tccaactcct aatctcaggt gatctaccca   2700

ccttggcctc ccaaattgct gggattacag gcgtgaacca ctgctccctt ccctgtcctt   2760

ctgattttgt aggtaaccac gtgcggaccg agcggccgca ggaacccta gtgatggagt    2820

tggccactcc ctctctgcgc gctcgctcgc tcactgaggc cgggcgacca aaggtcgccc   2880

gacgcccggg ctttgcccgg gcggcctcag tgagcgagcg agcgcgcagc tgcctgcagg   2940


<210> SEQ ID NO 4
<211> LENGTH: 724
<212> TYPE: PRT
<213> ORGANISM: Unknown
<220> FEATURE:
<223> OTHER INFORMATION: Natural sequence of the wild-type capsid AAV5
      protein VP1

<400> SEQUENCE: 4

Met Ser Phe Val Asp His Pro Pro Asp Trp Leu Glu Glu Val Gly Glu
1               5                   10                  15

Gly Leu Arg Glu Phe Leu Gly Leu Glu Ala Gly Pro Pro Lys Pro Lys
            20                  25                  30

Pro Asn Gln Gln His Gln Asp Gln Ala Arg Gly Leu Val Leu Pro Gly
        35                  40                  45

Tyr Asn Tyr Leu Gly Pro Gly Asn Gly Leu Asp Arg Gly Glu Pro Val
    50                  55                  60

Asn Arg Ala Asp Glu Val Ala Arg Glu His Asp Ile Ser Tyr Asn Glu
65                  70                  75                  80

Gln Leu Glu Ala Gly Asp Asn Pro Tyr Leu Lys Tyr Asn His Ala Asp
                85                  90                  95

Ala Glu Phe Gln Glu Lys Leu Ala Asp Asp Thr Ser Phe Gly Gly Asn
            100                 105                 110

Leu Gly Lys Ala Val Phe Gln Ala Lys Lys Arg Val Leu Glu Pro Phe
        115                 120                 125

Gly Leu Val Glu Glu Gly Ala Lys Thr Ala Pro Thr Gly Lys Arg Ile
    130                 135                 140

Asp Asp His Phe Pro Lys Arg Lys Lys Ala Arg Thr Glu Glu Asp Ser
145                 150                 155                 160

Lys Pro Ser Thr Ser Ser Asp Ala Glu Ala Gly Pro Ser Gly Ser Gln
                165                 170                 175

Gln Leu Gln Ile Pro Ala Gln Pro Ala Ser Ser Leu Gly Ala Asp Thr
            180                 185                 190

Met Ser Ala Gly Gly Gly Gly Pro Leu Gly Asp Asn Asn Gln Gly Ala
        195                 200                 205

Asp Gly Val Gly Asn Ala Ser Gly Asp Trp His Cys Asp Ser Thr Trp
    210                 215                 220

Met Gly Asp Arg Val Val Thr Lys Ser Thr Arg Thr Trp Val Leu Pro
225                 230                 235                 240

Ser Tyr Asn Asn His Gln Tyr Arg Glu Ile Lys Ser Gly Ser Val Asp
                245                 250                 255

Gly Ser Asn Ala Asn Ala Tyr Phe Gly Tyr Ser Thr Pro Trp Gly Tyr
            260                 265                 270

Phe Asp Phe Asn Arg Phe His Ser His Trp Ser Pro Arg Asp Trp Gln
        275                 280                 285
```

```
Arg Leu Ile Asn Asn Tyr Trp Gly Phe Arg Pro Arg Ser Leu Arg Val
    290                 295                 300

Lys Ile Phe Asn Ile Gln Val Lys Glu Val Thr Val Gln Asp Ser Thr
305                 310                 315                 320

Thr Thr Ile Ala Asn Asn Leu Thr Ser Thr Val Gln Val Phe Thr Asp
                325                 330                 335

Asp Asp Tyr Gln Leu Pro Tyr Val Val Gly Asn Gly Thr Glu Gly Cys
            340                 345                 350

Leu Pro Ala Phe Pro Pro Gln Val Phe Thr Leu Pro Gln Tyr Gly Tyr
        355                 360                 365

Ala Thr Leu Asn Arg Asp Asn Thr Glu Asn Pro Thr Glu Arg Ser Ser
    370                 375                 380

Phe Phe Cys Leu Glu Tyr Phe Pro Ser Lys Met Leu Arg Thr Gly Asn
385                 390                 395                 400

Asn Phe Glu Phe Thr Tyr Asn Phe Glu Glu Val Pro Phe His Ser Ser
                405                 410                 415

Phe Ala Pro Ser Gln Asn Leu Phe Lys Leu Ala Asn Pro Leu Val Asp
            420                 425                 430

Gln Tyr Leu Tyr Arg Phe Val Ser Thr Asn Asn Thr Gly Gly Val Gln
        435                 440                 445

Phe Asn Lys Asn Leu Ala Gly Arg Tyr Ala Asn Thr Tyr Lys Asn Trp
    450                 455                 460

Phe Pro Gly Pro Met Gly Arg Thr Gln Gly Trp Asn Leu Gly Ser Gly
465                 470                 475                 480

Val Asn Arg Ala Ser Val Ser Ala Phe Ala Thr Thr Asn Arg Met Glu
                485                 490                 495

Leu Glu Gly Ala Ser Tyr Gln Val Pro Pro Gln Pro Asn Gly Met Thr
            500                 505                 510

Asn Asn Leu Gln Gly Ser Asn Thr Tyr Ala Leu Glu Asn Thr Met Ile
        515                 520                 525

Phe Asn Ser Gln Pro Ala Asn Pro Gly Thr Thr Ala Thr Tyr Leu Glu
    530                 535                 540

Gly Asn Met Leu Ile Thr Ser Glu Ser Glu Thr Gln Pro Val Asn Arg
545                 550                 555                 560

Val Ala Tyr Asn Val Gly Gly Gln Met Ala Thr Asn Asn Gln Ser Ser
                565                 570                 575

Thr Thr Ala Pro Ala Thr Gly Thr Tyr Asn Leu Gln Glu Ile Val Pro
            580                 585                 590

Gly Ser Val Trp Met Glu Arg Asp Val Tyr Leu Gln Gly Pro Ile Trp
        595                 600                 605

Ala Lys Ile Pro Glu Thr Gly Ala His Phe His Pro Ser Pro Ala Met
    610                 615                 620

Gly Gly Phe Gly Leu Lys His Pro Pro Pro Met Met Leu Ile Lys Asn
625                 630                 635                 640

Thr Pro Val Pro Gly Asn Ile Thr Ser Phe Ser Asp Val Pro Val Ser
                645                 650                 655

Ser Phe Ile Thr Gln Tyr Ser Thr Gly Gln Val Thr Val Glu Met Glu
            660                 665                 670

Trp Glu Leu Lys Lys Glu Asn Ser Lys Arg Trp Asn Pro Glu Ile Gln
        675                 680                 685

Tyr Thr Asn Asn Tyr Asn Asp Pro Gln Phe Val Asp Phe Ala Pro Asp
    690                 695                 700

Ser Thr Gly Glu Tyr Arg Thr Thr Arg Pro Ile Gly Thr Arg Tyr Leu
```

```
705                 710                 715                 720

Thr Arg Pro Leu


<210> SEQ ID NO 5
<211> LENGTH: 724
<212> TYPE: PRT
<213> ORGANISM: Artificial sequence
<220> FEATURE:
<223> OTHER INFORMATION: modified VP1 protein of AAV5 capsid with S2A
      and T711S substitutions

<400> SEQUENCE: 5

Met Ala Phe Val Asp His Pro Pro Asp Trp Leu Glu Glu Val Gly Glu
1               5                   10                  15

Gly Leu Arg Glu Phe Leu Gly Leu Glu Ala Gly Pro Pro Lys Pro Lys
            20                  25                  30

Pro Asn Gln Gln His Gln Asp Gln Ala Arg Gly Leu Val Leu Pro Gly
        35                  40                  45

Tyr Asn Tyr Leu Gly Pro Gly Asn Gly Leu Asp Arg Gly Glu Pro Val
    50                  55                  60

Asn Arg Ala Asp Glu Val Ala Arg Glu His Asp Ile Ser Tyr Asn Glu
65                  70                  75                  80

Gln Leu Glu Ala Gly Asp Asn Pro Tyr Leu Lys Tyr Asn His Ala Asp
                85                  90                  95

Ala Glu Phe Gln Glu Lys Leu Ala Asp Asp Thr Ser Phe Gly Gly Asn
            100                 105                 110

Leu Gly Lys Ala Val Phe Gln Ala Lys Lys Arg Val Leu Glu Pro Phe
        115                 120                 125

Gly Leu Val Glu Glu Gly Ala Lys Thr Ala Pro Thr Gly Lys Arg Ile
    130                 135                 140

Asp Asp His Phe Pro Lys Arg Lys Lys Ala Arg Thr Glu Glu Asp Ser
145                 150                 155                 160

Lys Pro Ser Thr Ser Ser Asp Ala Glu Ala Gly Pro Ser Gly Ser Gln
                165                 170                 175

Gln Leu Gln Ile Pro Ala Gln Pro Ala Ser Ser Leu Gly Ala Asp Thr
            180                 185                 190

Met Ser Ala Gly Gly Gly Gly Pro Leu Gly Asp Asn Asn Gln Gly Ala
        195                 200                 205

Asp Gly Val Gly Asn Ala Ser Gly Asp Trp His Cys Asp Ser Thr Trp
    210                 215                 220

Met Gly Asp Arg Val Val Thr Lys Ser Thr Arg Thr Trp Val Leu Pro
225                 230                 235                 240

Ser Tyr Asn Asn His Gln Tyr Arg Glu Ile Lys Ser Gly Ser Val Asp
                245                 250                 255

Gly Ser Asn Ala Asn Ala Tyr Phe Gly Tyr Ser Thr Pro Trp Gly Tyr
            260                 265                 270

Phe Asp Phe Asn Arg Phe His Ser His Trp Ser Pro Arg Asp Trp Gln
        275                 280                 285

Arg Leu Ile Asn Asn Tyr Trp Gly Phe Arg Pro Arg Ser Leu Arg Val
    290                 295                 300

Lys Ile Phe Asn Ile Gln Val Lys Glu Val Thr Val Gln Asp Ser Thr
305                 310                 315                 320

Thr Thr Ile Ala Asn Asn Leu Thr Ser Thr Val Gln Val Phe Thr Asp
                325                 330                 335

Asp Asp Tyr Gln Leu Pro Tyr Val Val Gly Asn Gly Thr Glu Gly Cys
```

```
            340                 345                 350

Leu Pro Ala Phe Pro Pro Gln Val Phe Thr Leu Pro Gln Tyr Gly Tyr
        355                 360                 365

Ala Thr Leu Asn Arg Asp Asn Thr Glu Asn Pro Thr Glu Arg Ser Ser
    370                 375                 380

Phe Phe Cys Leu Glu Tyr Phe Pro Ser Lys Met Leu Arg Thr Gly Asn
385                 390                 395                 400

Asn Phe Glu Phe Thr Tyr Asn Phe Glu Glu Val Pro Phe His Ser Ser
                405                 410                 415

Phe Ala Pro Ser Gln Asn Leu Phe Lys Leu Ala Asn Pro Leu Val Asp
            420                 425                 430

Gln Tyr Leu Tyr Arg Phe Val Ser Thr Asn Asn Thr Gly Gly Val Gln
        435                 440                 445

Phe Asn Lys Asn Leu Ala Gly Arg Tyr Ala Asn Thr Tyr Lys Asn Trp
    450                 455                 460

Phe Pro Gly Pro Met Gly Arg Thr Gln Gly Trp Asn Leu Gly Ser Gly
465                 470                 475                 480

Val Asn Arg Ala Ser Val Ser Ala Phe Ala Thr Thr Asn Arg Met Glu
                485                 490                 495

Leu Glu Gly Ala Ser Tyr Gln Val Pro Pro Gln Pro Asn Gly Met Thr
            500                 505                 510

Asn Asn Leu Gln Gly Ser Asn Thr Tyr Ala Leu Glu Asn Thr Met Ile
        515                 520                 525

Phe Asn Ser Gln Pro Ala Asn Pro Gly Thr Thr Ala Thr Tyr Leu Glu
    530                 535                 540

Gly Asn Met Leu Ile Thr Ser Glu Ser Glu Thr Gln Pro Val Asn Arg
545                 550                 555                 560

Val Ala Tyr Asn Val Gly Gly Gln Met Ala Thr Asn Asn Gln Ser Ser
                565                 570                 575

Thr Thr Ala Pro Ala Thr Gly Thr Tyr Asn Leu Gln Glu Ile Val Pro
            580                 585                 590

Gly Ser Val Trp Met Glu Arg Asp Val Tyr Leu Gln Gly Pro Ile Trp
        595                 600                 605

Ala Lys Ile Pro Glu Thr Gly Ala His Phe His Pro Ser Pro Ala Met
    610                 615                 620

Gly Gly Phe Gly Leu Lys His Pro Pro Pro Met Met Leu Ile Lys Asn
625                 630                 635                 640

Thr Pro Val Pro Gly Asn Ile Thr Ser Phe Ser Asp Val Pro Val Ser
                645                 650                 655

Ser Phe Ile Thr Gln Tyr Ser Thr Gly Gln Val Thr Val Glu Met Glu
            660                 665                 670

Trp Glu Leu Lys Lys Glu Asn Ser Lys Arg Trp Asn Pro Glu Ile Gln
        675                 680                 685

Tyr Thr Asn Asn Tyr Asn Asp Pro Gln Phe Val Asp Phe Ala Pro Asp
    690                 695                 700

Ser Thr Gly Glu Tyr Arg Ser Thr Arg Pro Ile Gly Thr Arg Tyr Leu
705                 710                 715                 720

Thr Arg Pro Leu
```

<210> SEQ ID NO 6
<211> LENGTH: 1273
<212> TYPE: PRT
<213> ORGANISM: Betacoronavirus SARS related coronavirus

<400> SEQUENCE: 6

```
Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Asp Pro Phe Leu Gly Val Tyr
    130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
        195                 200                 205

Pro Ile Asn Leu Val Arg Asp Leu Pro Gln Gly Phe Ser Ala Leu Glu
    210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
        275                 280                 285

Val Asp Cys Ala Leu Asp Pro Leu Ser Glu Thr Lys Cys Thr Leu Lys
    290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                325                 330                 335

Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
        355                 360                 365

Tyr Asn Ser Ala Ser Phe Ser Thr Phe Lys Cys Tyr Gly Val Ser Pro
    370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415
```

```
Lys Ile Ala Asp Tyr Asn Tyr Lys Leu Pro Asp Asp Phe Thr Gly Cys
            420                 425                 430

Val Ile Ala Trp Asn Ser Asn Asn Leu Asp Ser Lys Val Gly Gly Asn
        435                 440                 445

Tyr Asn Tyr Leu Tyr Arg Leu Phe Arg Lys Ser Asn Leu Lys Pro Phe
    450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
                485                 490                 495

Phe Gln Pro Thr Asn Gly Val Gly Tyr Gln Pro Tyr Arg Val Val Val
            500                 505                 510

Leu Ser Phe Glu Leu Leu His Ala Pro Ala Thr Val Cys Gly Pro Lys
        515                 520                 525

Lys Ser Thr Asn Leu Val Lys Asn Lys Cys Val Asn Phe Asn Phe Asn
    530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
                565                 570                 575

Arg Asp Pro Gln Thr Leu Glu Ile Leu Asp Ile Thr Pro Cys Ser Phe
            580                 585                 590

Gly Gly Val Ser Val Ile Thr Pro Gly Thr Asn Thr Ser Asn Gln Val
        595                 600                 605

Ala Val Leu Tyr Gln Asp Val Asn Cys Thr Glu Val Pro Val Ala Ile
    610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
                645                 650                 655

Asn Asn Ser Tyr Glu Cys Asp Ile Pro Ile Gly Ala Gly Ile Cys Ala
            660                 665                 670

Ser Tyr Gln Thr Gln Thr Asn Ser Pro Arg Arg Ala Arg Ser Val Ala
        675                 680                 685

Ser Gln Ser Ile Ile Ala Tyr Thr Met Ser Leu Gly Ala Glu Asn Ser
    690                 695                 700

Val Ala Tyr Ser Asn Asn Ser Ile Ala Ile Pro Thr Asn Phe Thr Ile
705                 710                 715                 720

Ser Val Thr Thr Glu Ile Leu Pro Val Ser Met Thr Lys Thr Ser Val
                725                 730                 735

Asp Cys Thr Met Tyr Ile Cys Gly Asp Ser Thr Glu Cys Ser Asn Leu
            740                 745                 750

Leu Leu Gln Tyr Gly Ser Phe Cys Thr Gln Leu Asn Arg Ala Leu Thr
        755                 760                 765

Gly Ile Ala Val Glu Gln Asp Lys Asn Thr Gln Glu Val Phe Ala Gln
    770                 775                 780

Val Lys Gln Ile Tyr Lys Thr Pro Pro Ile Lys Asp Phe Gly Gly Phe
785                 790                 795                 800

Asn Phe Ser Gln Ile Leu Pro Asp Pro Ser Lys Pro Ser Lys Arg Ser
                805                 810                 815

Phe Ile Glu Asp Leu Leu Phe Asn Lys Val Thr Leu Ala Asp Ala Gly
            820                 825                 830
```

```
Phe Ile Lys Gln Tyr Gly Asp Cys Leu Gly Asp Ile Ala Ala Arg Asp
        835                 840                 845

Leu Ile Cys Ala Gln Lys Phe Asn Gly Leu Thr Val Leu Pro Pro Leu
    850                 855                 860

Leu Thr Asp Glu Met Ile Ala Gln Tyr Thr Ser Ala Leu Leu Ala Gly
865                 870                 875                 880

Thr Ile Thr Ser Gly Trp Thr Phe Gly Ala Gly Ala Ala Leu Gln Ile
                885                 890                 895

Pro Phe Ala Met Gln Met Ala Tyr Arg Phe Asn Gly Ile Gly Val Thr
            900                 905                 910

Gln Asn Val Leu Tyr Glu Asn Gln Lys Leu Ile Ala Asn Gln Phe Asn
        915                 920                 925

Ser Ala Ile Gly Lys Ile Gln Asp Ser Leu Ser Ser Thr Ala Ser Ala
    930                 935                 940

Leu Gly Lys Leu Gln Asp Val Val Asn Gln Asn Ala Gln Ala Leu Asn
945                 950                 955                 960

Thr Leu Val Lys Gln Leu Ser Ser Asn Phe Gly Ala Ile Ser Ser Val
                965                 970                 975

Leu Asn Asp Ile Leu Ser Arg Leu Asp Lys Val Glu Ala Glu Val Gln
            980                 985                 990

Ile Asp Arg Leu Ile Thr Gly Arg Leu Gln Ser Leu Gln Thr Tyr Val
        995                 1000                1005

Thr Gln Gln Leu Ile Arg Ala Ala Glu Ile Arg Ala Ser Ala Asn Leu
    1010                1015                1020

Ala Ala Thr Lys Met Ser Glu Cys Val Leu Gly Gln Ser Lys Arg Val
1025                1030                1035                1040

Asp Phe Cys Gly Lys Gly Tyr His Leu Met Ser Phe Pro Gln Ser Ala
                1045                1050                1055

Pro His Gly Val Val Phe Leu His Val Thr Tyr Val Pro Ala Gln Glu
            1060                1065                1070

Lys Asn Phe Thr Thr Ala Pro Ala Ile Cys His Asp Gly Lys Ala His
        1075                1080                1085

Phe Pro Arg Glu Gly Val Phe Val Ser Asn Gly Thr His Trp Phe Val
    1090                1095                1100

Thr Gln Arg Asn Phe Tyr Glu Pro Gln Ile Ile Thr Thr Asp Asn Thr
1105                1110                1115                1120

Phe Val Ser Gly Asn Cys Asp Val Val Ile Gly Ile Val Asn Asn Thr
                1125                1130                1135

Val Tyr Asp Pro Leu Gln Pro Glu Leu Asp Ser Phe Lys Glu Glu Leu
            1140                1145                1150

Asp Lys Tyr Phe Lys Asn His Thr Ser Pro Asp Val Asp Leu Gly Asp
        1155                1160                1165

Ile Ser Gly Ile Asn Ala Ser Val Val Asn Ile Gln Lys Glu Ile Asp
    1170                1175                1180

Arg Leu Asn Glu Val Ala Lys Asn Leu Asn Glu Ser Leu Ile Asp Leu
1185                1190                1195                1200

Gln Glu Leu Gly Lys Tyr Glu Gln Tyr Ile Lys Trp Pro Trp Tyr Ile
                1205                1210                1215

Trp Leu Gly Phe Ile Ala Gly Leu Ile Ala Ile Val Met Val Thr Ile
            1220                1225                1230

Met Leu Cys Cys Met Thr Ser Cys Cys Ser Cys Leu Lys Gly Cys Cys
        1235                1240                1245

Ser Cys Gly Ser Cys Cys Lys Phe Asp Glu Asp Asp Ser Glu Pro Val
```

```
    1250                1255                1260

Leu Lys Gly Val Lys Leu His Tyr Thr
1265                1270


<210> SEQ ID NO 7
<211> LENGTH: 278
<212> TYPE: PRT
<213> ORGANISM: Betacoronavirus SARS related coronavirus

<400> SEQUENCE: 7

Arg Val Gln Pro Thr Glu Ser Ile Val Arg Phe Pro Asn Ile Thr Asn
1               5                   10                  15

Leu Cys Pro Phe Gly Glu Val Phe Asn Ala Thr Arg Phe Ala Ser Val
            20                  25                  30

Tyr Ala Trp Asn Arg Lys Arg Ile Ser Asn Cys Val Ala Asp Tyr Ser
        35                  40                  45

Val Leu Tyr Asn Ser Ala Ser Phe Ser Thr Phe Lys Cys Tyr Gly Val
    50                  55                  60

Ser Pro Thr Lys Leu Asn Asp Leu Cys Phe Thr Asn Val Tyr Ala Asp
65                  70                  75                  80

Ser Phe Val Ile Arg Gly Asp Glu Val Arg Gln Ile Ala Pro Gly Gln
                85                  90                  95

Thr Gly Lys Ile Ala Asp Tyr Asn Tyr Lys Leu Pro Asp Asp Phe Thr
            100                 105                 110

Gly Cys Val Ile Ala Trp Asn Ser Asn Asn Leu Asp Ser Lys Val Gly
        115                 120                 125

Gly Asn Tyr Asn Tyr Leu Tyr Arg Leu Phe Arg Lys Ser Asn Leu Lys
    130                 135                 140

Pro Phe Glu Arg Asp Ile Ser Thr Glu Ile Tyr Gln Ala Gly Ser Thr
145                 150                 155                 160

Pro Cys Asn Gly Val Glu Gly Phe Asn Cys Tyr Phe Pro Leu Gln Ser
                165                 170                 175

Tyr Gly Phe Gln Pro Thr Asn Gly Val Gly Tyr Gln Pro Tyr Arg Val
            180                 185                 190

Val Val Leu Ser Phe Glu Leu Leu His Ala Pro Ala Thr Val Cys Gly
        195                 200                 205

Pro Lys Lys Ser Thr Asn Leu Val Lys Asn Lys Cys Val Asn Phe Asn
    210                 215                 220

Phe Asn Gly Leu Thr Gly Thr Gly Val Leu Thr Glu Ser Asn Lys Lys
225                 230                 235                 240

Phe Leu Pro Phe Gln Gln Phe Gly Arg Asp Ile Ala Asp Thr Thr Asp
                245                 250                 255

Ala Val Arg Asp Pro Gln Thr Leu Glu Ile Leu Asp Ile Thr Pro Cys
            260                 265                 270

Ser Phe Gly Gly Val Ser
        275


<210> SEQ ID NO 8
<211> LENGTH: 130
<212> TYPE: DNA
<213> ORGANISM: Unknown
<220> FEATURE:
<223> OTHER INFORMATION: left (first) ITR (inverted tail repeats)

<400> SEQUENCE: 8

cctgcaggca gctgcgcgct cgctcgctca ctgaggccgc ccgggcgtcg ggcgaccttt     60
```

ggtcgcccgg cctcagtgag cgagcgagcg cgcagagagg gagtggccaa ctccatcact 120
aggggttcct 130

<210> SEQ ID NO 9
<211> LENGTH: 304
<212> TYPE: DNA
<213> ORGANISM: Unknown
<220> FEATURE:
<223> OTHER INFORMATION: CMV (cytomegalovirus) enhancer

<400> SEQUENCE: 9
cgttacataa cttacggtaa atggcccgcc tggctgaccg cccaacgacc cccgcccatt 60
gacgtcaata atgacgtatg ttcccatagt aacgccaata gggactttcc attgacgtca 120
atgggtggag tatttacggt aaactgccca cttggcagta catcaagtgt atcatatgcc 180
aagtacgccc cctattgacg tcaatgacgg taaatggccc gcctggcatt atgcccagta 240
catgacctta tgggactttc ctacttggca gtacatctac gtattagtca tcgctattac 300
catg 304

<210> SEQ ID NO 10
<211> LENGTH: 204
<212> TYPE: DNA
<213> ORGANISM: Unknown
<220> FEATURE:
<223> OTHER INFORMATION: CMV (cytomegalovirus) promoter

<400> SEQUENCE: 10
gtgatgcggt tttggcagta catcaatggg cgtggatagc ggtttgactc acggggattt 60
ccaagtctcc accccattga cgtcaatggg agtttgtttt ggcaccaaaa tcaacgggac 120
tttccaaaat gtcgtaacaa ctccgcccca ttgacgcaaa tgggcggtag gcgtgtacgg 180
tgggaggtct atataagcag agct 204

<210> SEQ ID NO 11
<211> LENGTH: 493
<212> TYPE: DNA
<213> ORGANISM: Unknown
<220> FEATURE:
<223> OTHER INFORMATION: hBG1 gene intron (hemoglobin gamma-1 subunit gene)

<400> SEQUENCE: 11
cgaatcccgg ccgggaacgg tgcattggaa cgcggattcc ccgtgccaag agtgacgtaa 60
gtaccgccta tagagtctat aggcccacaa aaaatgcttt cttcttttaa tatacttttt 120
tgtttatctt atttctaata ctttccctaa tctctttctt tcagggcaat aatgatacaa 180
tgtatcatgc ctctttgcac cattctaaag aataacagtg ataatttctg ggttaaggca 240
atagcaatat ttctgcatat aaatatttct gcatataaat tgtaactgat gtaagaggtt 300
tcatattgct aatagcagct acaatccagc taccattctg cttttatttt atggttggga 360
taaggctgga ttattctgag tccaagctag gcccttttgc taatcatgtt catacctctt 420
atcttcctcc cacagctcct gggcaacgtg ctggtctgtg tgctggccca tcactttggc 480
aaagaattgg gat 493

<210> SEQ ID NO 12
<211> LENGTH: 479
<212> TYPE: DNA
<213> ORGANISM: Unknown
<220> FEATURE:

<223> OTHER INFORMATION: hGH1 (human growth hormone gene) polyadenylation signal

<400> SEQUENCE: 12

```
acgggtggca tccctgtgac ccctccccag tgcctctcct ggccctggaa gttgccactc     60

cagtgcccac cagccttgtc ctaataaaat taagttgcat cattttgtct gactaggtgt    120

ccttctataa tattatgggg tggagggggg tggtatggag caaggggcaa gttgggaaga    180

caacctgtag ggcctgcggg gtctattggg aaccaagctg gagtgcagtg gcacaatctt    240

ggctcactgc aatctccgcc tcctgggttc aagcgattct cctgcctcag cctcccgagt    300

tgttgggatt ccaggcatgc atgaccaggc tcagctaatt tttgtttttt tggtagagac    360

ggggtttcac catattggcc aggctggtct ccaactccta atctcaggtg atctacccac    420

cttggcctcc caaattgctg ggattacagg cgtgaaccac tgctcccttc cctgtcctt     479
```

<210> SEQ ID NO 13
<211> LENGTH: 141
<212> TYPE: DNA
<213> ORGANISM: Unknown
<220> FEATURE:
<223> OTHER INFORMATION: right (second) ITR

<400> SEQUENCE: 13

```
aggaacccct agtgatggag ttggccactc cctctctgcg cgctcgctcg ctcactgagg     60

ccgggcgacc aaaggtcgcc cgacgcccgg gctttgcccg ggcggcctca gtgagcgagc    120

gagcgcgcag ctgcctgcag g                                              141
```

<210> SEQ ID NO 14
<211> LENGTH: 588
<212> TYPE: PRT
<213> ORGANISM: Unknown
<220> FEATURE:
<223> OTHER INFORMATION: Natural sequence of the VP2 protein of the wild-type AAV5 capsid

<400> SEQUENCE: 14

```
Thr Ala Pro Thr Gly Lys Arg Ile Asp Asp His Phe Pro Lys Arg Lys
1               5                   10                  15

Lys Ala Arg Thr Glu Glu Asp Ser Lys Pro Ser Thr Ser Ser Asp Ala
            20                  25                  30

Glu Ala Gly Pro Ser Gly Ser Gln Gln Leu Gln Ile Pro Ala Gln Pro
        35                  40                  45

Ala Ser Ser Leu Gly Ala Asp Thr Met Ser Ala Gly Gly Gly Gly Pro
    50                  55                  60

Leu Gly Asp Asn Asn Gln Gly Ala Asp Gly Val Gly Asn Ala Ser Gly
65                  70                  75                  80

Asp Trp His Cys Asp Ser Thr Trp Met Gly Asp Arg Val Val Thr Lys
                85                  90                  95

Ser Thr Arg Thr Trp Val Leu Pro Ser Tyr Asn Asn His Gln Tyr Arg
            100                 105                 110

Glu Ile Lys Ser Gly Ser Val Asp Gly Ser Asn Ala Asn Ala Tyr Phe
        115                 120                 125

Gly Tyr Ser Thr Pro Trp Gly Tyr Phe Asp Phe Asn Arg Phe His Ser
    130                 135                 140

His Trp Ser Pro Arg Asp Trp Gln Arg Leu Ile Asn Asn Tyr Trp Gly
145                 150                 155                 160

Phe Arg Pro Arg Ser Leu Arg Val Lys Ile Phe Asn Ile Gln Val Lys
```

```
                165                 170                 175

Glu Val Thr Val Gln Asp Ser Thr Thr Thr Ile Ala Asn Asn Leu Thr
            180                 185                 190

Ser Thr Val Gln Val Phe Thr Asp Asp Asp Tyr Gln Leu Pro Tyr Val
        195                 200                 205

Val Gly Asn Gly Thr Glu Gly Cys Leu Pro Ala Phe Pro Pro Gln Val
    210                 215                 220

Phe Thr Leu Pro Gln Tyr Gly Tyr Ala Thr Leu Asn Arg Asp Asn Thr
225                 230                 235                 240

Glu Asn Pro Thr Glu Arg Ser Ser Phe Phe Cys Leu Glu Tyr Phe Pro
                245                 250                 255

Ser Lys Met Leu Arg Thr Gly Asn Asn Phe Glu Phe Thr Tyr Asn Phe
            260                 265                 270

Glu Glu Val Pro Phe His Ser Ser Phe Ala Pro Ser Gln Asn Leu Phe
        275                 280                 285

Lys Leu Ala Asn Pro Leu Val Asp Gln Tyr Leu Tyr Arg Phe Val Ser
    290                 295                 300

Thr Asn Asn Thr Gly Gly Val Gln Phe Asn Lys Asn Leu Ala Gly Arg
305                 310                 315                 320

Tyr Ala Asn Thr Tyr Lys Asn Trp Phe Pro Gly Pro Met Gly Arg Thr
                325                 330                 335

Gln Gly Trp Asn Leu Gly Ser Gly Val Asn Arg Ala Ser Val Ser Ala
            340                 345                 350

Phe Ala Thr Thr Asn Arg Met Glu Leu Glu Gly Ala Ser Tyr Gln Val
        355                 360                 365

Pro Pro Gln Pro Asn Gly Met Thr Asn Asn Leu Gln Gly Ser Asn Thr
    370                 375                 380

Tyr Ala Leu Glu Asn Thr Met Ile Phe Asn Ser Gln Pro Ala Asn Pro
385                 390                 395                 400

Gly Thr Thr Ala Thr Tyr Leu Glu Gly Asn Met Leu Ile Thr Ser Glu
                405                 410                 415

Ser Glu Thr Gln Pro Val Asn Arg Val Ala Tyr Asn Val Gly Gly Gln
            420                 425                 430

Met Ala Thr Asn Asn Gln Ser Ser Thr Thr Ala Pro Ala Thr Gly Thr
        435                 440                 445

Tyr Asn Leu Gln Glu Ile Val Pro Gly Ser Val Trp Met Glu Arg Asp
    450                 455                 460

Val Tyr Leu Gln Gly Pro Ile Trp Ala Lys Ile Pro Glu Thr Gly Ala
465                 470                 475                 480

His Phe His Pro Ser Pro Ala Met Gly Gly Phe Gly Leu Lys His Pro
                485                 490                 495

Pro Pro Met Met Leu Ile Lys Asn Thr Pro Val Pro Gly Asn Ile Thr
            500                 505                 510

Ser Phe Ser Asp Val Pro Val Ser Ser Phe Ile Thr Gln Tyr Ser Thr
        515                 520                 525

Gly Gln Val Thr Val Glu Met Glu Trp Glu Leu Lys Lys Glu Asn Ser
    530                 535                 540

Lys Arg Trp Asn Pro Glu Ile Gln Tyr Thr Asn Asn Tyr Asn Asp Pro
545                 550                 555                 560

Gln Phe Val Asp Phe Ala Pro Asp Ser Thr Gly Glu Tyr Arg Thr Thr
                565                 570                 575

Arg Pro Ile Gly Thr Arg Tyr Leu Thr Arg Pro Leu
            580                 585
```

<210> SEQ ID NO 15
<211> LENGTH: 532
<212> TYPE: PRT
<213> ORGANISM: Unknown
<220> FEATURE:
<223> OTHER INFORMATION: Natural sequence of the VP3 protein of the wild-type AAV5 capsid

<400> SEQUENCE: 15

```
Met Ser Ala Gly Gly Gly Gly Pro Leu Gly Asp Asn Asn Gln Gly Ala
1               5                   10                  15

Asp Gly Val Gly Asn Ala Ser Gly Asp Trp His Cys Asp Ser Thr Trp
            20                  25                  30

Met Gly Asp Arg Val Val Thr Lys Ser Thr Arg Thr Trp Val Leu Pro
        35                  40                  45

Ser Tyr Asn Asn His Gln Tyr Arg Glu Ile Lys Ser Gly Ser Val Asp
    50                  55                  60

Gly Ser Asn Ala Asn Ala Tyr Phe Gly Tyr Ser Thr Pro Trp Gly Tyr
65                  70                  75                  80

Phe Asp Phe Asn Arg Phe His Ser His Trp Ser Pro Arg Asp Trp Gln
                85                  90                  95

Arg Leu Ile Asn Asn Tyr Trp Gly Phe Arg Pro Arg Ser Leu Arg Val
            100                 105                 110

Lys Ile Phe Asn Ile Gln Val Lys Glu Val Thr Val Gln Asp Ser Thr
        115                 120                 125

Thr Thr Ile Ala Asn Asn Leu Thr Ser Thr Val Gln Val Phe Thr Asp
    130                 135                 140

Asp Asp Tyr Gln Leu Pro Tyr Val Val Gly Asn Gly Thr Glu Gly Cys
145                 150                 155                 160

Leu Pro Ala Phe Pro Pro Gln Val Phe Thr Leu Pro Gln Tyr Gly Tyr
                165                 170                 175

Ala Thr Leu Asn Arg Asp Asn Thr Glu Asn Pro Thr Glu Arg Ser Ser
            180                 185                 190

Phe Phe Cys Leu Glu Tyr Phe Pro Ser Lys Met Leu Arg Thr Gly Asn
        195                 200                 205

Asn Phe Glu Phe Thr Tyr Asn Phe Glu Glu Val Pro Phe His Ser Ser
    210                 215                 220

Phe Ala Pro Ser Gln Asn Leu Phe Lys Leu Ala Asn Pro Leu Val Asp
225                 230                 235                 240

Gln Tyr Leu Tyr Arg Phe Val Ser Thr Asn Asn Thr Gly Gly Val Gln
                245                 250                 255

Phe Asn Lys Asn Leu Ala Gly Arg Tyr Ala Asn Thr Tyr Lys Asn Trp
            260                 265                 270

Phe Pro Gly Pro Met Gly Arg Thr Gln Gly Trp Asn Leu Gly Ser Gly
        275                 280                 285

Val Asn Arg Ala Ser Val Ser Ala Phe Ala Thr Thr Asn Arg Met Glu
    290                 295                 300

Leu Glu Gly Ala Ser Tyr Gln Val Pro Pro Gln Pro Asn Gly Met Thr
305                 310                 315                 320

Asn Asn Leu Gln Gly Ser Asn Thr Tyr Ala Leu Glu Asn Thr Met Ile
                325                 330                 335

Phe Asn Ser Gln Pro Ala Asn Pro Gly Thr Thr Ala Thr Tyr Leu Glu
            340                 345                 350

Gly Asn Met Leu Ile Thr Ser Glu Ser Glu Thr Gln Pro Val Asn Arg
```

```
        355                 360                 365

Val Ala Tyr Asn Val Gly Gly Gln Met Ala Thr Asn Asn Gln Ser Ser
    370                 375                 380

Thr Thr Ala Pro Ala Thr Gly Thr Tyr Asn Leu Gln Glu Ile Val Pro
385                 390                 395                 400

Gly Ser Val Trp Met Glu Arg Asp Val Tyr Leu Gln Gly Pro Ile Trp
                405                 410                 415

Ala Lys Ile Pro Glu Thr Gly Ala His Phe His Pro Ser Pro Ala Met
            420                 425                 430

Gly Gly Phe Gly Leu Lys His Pro Pro Pro Met Met Leu Ile Lys Asn
        435                 440                 445

Thr Pro Val Pro Gly Asn Ile Thr Ser Phe Ser Asp Val Pro Val Ser
    450                 455                 460

Ser Phe Ile Thr Gln Tyr Ser Thr Gly Gln Val Thr Val Glu Met Glu
465                 470                 475                 480

Trp Glu Leu Lys Lys Glu Asn Ser Lys Arg Trp Asn Pro Glu Ile Gln
                485                 490                 495

Tyr Thr Asn Asn Tyr Asn Asp Pro Gln Phe Val Asp Phe Ala Pro Asp
            500                 505                 510

Ser Thr Gly Glu Tyr Arg Thr Thr Arg Pro Ile Gly Thr Arg Tyr Leu
        515                 520                 525

Thr Arg Pro Leu
    530


<210> SEQ ID NO 16
<211> LENGTH: 588
<212> TYPE: PRT
<213> ORGANISM: Unknown
<220> FEATURE:
<223> OTHER INFORMATION: isolated modified protein VP2 - AAV5 capsid
      with replacement T575S

<400> SEQUENCE: 16

Thr Ala Pro Thr Gly Lys Arg Ile Asp Asp His Phe Pro Lys Arg Lys
1               5                   10                  15

Lys Ala Arg Thr Glu Glu Asp Ser Lys Pro Ser Thr Ser Ser Asp Ala
            20                  25                  30

Glu Ala Gly Pro Ser Gly Ser Gln Gln Leu Gln Ile Pro Ala Gln Pro
        35                  40                  45

Ala Ser Ser Leu Gly Ala Asp Thr Met Ser Ala Gly Gly Gly Gly Pro
    50                  55                  60

Leu Gly Asp Asn Asn Gln Gly Ala Asp Gly Val Gly Asn Ala Ser Gly
65                  70                  75                  80

Asp Trp His Cys Asp Ser Thr Trp Met Gly Asp Arg Val Val Thr Lys
                85                  90                  95

Ser Thr Arg Thr Trp Val Leu Pro Ser Tyr Asn Asn His Gln Tyr Arg
            100                 105                 110

Glu Ile Lys Ser Gly Ser Val Asp Gly Ser Asn Ala Asn Ala Tyr Phe
        115                 120                 125

Gly Tyr Ser Thr Pro Trp Gly Tyr Phe Asp Phe Asn Arg Phe His Ser
    130                 135                 140

His Trp Ser Pro Arg Asp Trp Gln Arg Leu Ile Asn Asn Tyr Trp Gly
145                 150                 155                 160

Phe Arg Pro Arg Ser Leu Arg Val Lys Ile Phe Asn Ile Gln Val Lys
                165                 170                 175
```

-continued

```
Glu Val Thr Val Gln Asp Ser Thr Thr Thr Ile Ala Asn Asn Leu Thr
            180                 185                 190

Ser Thr Val Gln Val Phe Thr Asp Asp Asp Tyr Gln Leu Pro Tyr Val
        195                 200                 205

Val Gly Asn Gly Thr Glu Gly Cys Leu Pro Ala Phe Pro Pro Gln Val
    210                 215                 220

Phe Thr Leu Pro Gln Tyr Gly Tyr Ala Thr Leu Asn Arg Asp Asn Thr
225                 230                 235                 240

Glu Asn Pro Thr Glu Arg Ser Ser Phe Phe Cys Leu Glu Tyr Phe Pro
                245                 250                 255

Ser Lys Met Leu Arg Thr Gly Asn Asn Phe Glu Phe Thr Tyr Asn Phe
            260                 265                 270

Glu Glu Val Pro Phe His Ser Ser Phe Ala Pro Ser Gln Asn Leu Phe
        275                 280                 285

Lys Leu Ala Asn Pro Leu Val Asp Gln Tyr Leu Tyr Arg Phe Val Ser
    290                 295                 300

Thr Asn Asn Thr Gly Gly Val Gln Phe Asn Lys Asn Leu Ala Gly Arg
305                 310                 315                 320

Tyr Ala Asn Thr Tyr Lys Asn Trp Phe Pro Gly Pro Met Gly Arg Thr
                325                 330                 335

Gln Gly Trp Asn Leu Gly Ser Gly Val Asn Arg Ala Ser Val Ser Ala
            340                 345                 350

Phe Ala Thr Thr Asn Arg Met Glu Leu Glu Gly Ala Ser Tyr Gln Val
        355                 360                 365

Pro Pro Gln Pro Asn Gly Met Thr Asn Asn Leu Gln Gly Ser Asn Thr
    370                 375                 380

Tyr Ala Leu Glu Asn Thr Met Ile Phe Asn Ser Gln Pro Ala Asn Pro
385                 390                 395                 400

Gly Thr Thr Ala Thr Tyr Leu Glu Gly Asn Met Leu Ile Thr Ser Glu
                405                 410                 415

Ser Glu Thr Gln Pro Val Asn Arg Val Ala Tyr Asn Val Gly Gly Gln
            420                 425                 430

Met Ala Thr Asn Asn Gln Ser Ser Thr Thr Ala Pro Ala Thr Gly Thr
        435                 440                 445

Tyr Asn Leu Gln Glu Ile Val Pro Gly Ser Val Trp Met Glu Arg Asp
    450                 455                 460

Val Tyr Leu Gln Gly Pro Ile Trp Ala Lys Ile Pro Glu Thr Gly Ala
465                 470                 475                 480

His Phe His Pro Ser Pro Ala Met Gly Gly Phe Gly Leu Lys His Pro
                485                 490                 495

Pro Pro Met Met Leu Ile Lys Asn Thr Pro Val Pro Gly Asn Ile Thr
            500                 505                 510

Ser Phe Ser Asp Val Pro Val Ser Ser Phe Ile Thr Gln Tyr Ser Thr
        515                 520                 525

Gly Gln Val Thr Val Glu Met Glu Trp Glu Leu Lys Lys Glu Asn Ser
    530                 535                 540

Lys Arg Trp Asn Pro Glu Ile Gln Tyr Thr Asn Asn Tyr Asn Asp Pro
545                 550                 555                 560

Gln Phe Val Asp Phe Ala Pro Asp Ser Thr Gly Glu Tyr Arg Ser Thr
                565                 570                 575

Arg Pro Ile Gly Thr Arg Tyr Leu Thr Arg Pro Leu
            580                 585
```

```
<210> SEQ ID NO 17
<211> LENGTH: 532
<212> TYPE: PRT
<213> ORGANISM: Unknown
<220> FEATURE:
<223> OTHER INFORMATION: isolated modified protein VP3 - AAV5 capsid
      with replacement T519S

<400> SEQUENCE: 17

Met Ser Ala Gly Gly Gly Gly Pro Leu Gly Asp Asn Asn Gln Gly Ala
1               5                   10                  15

Asp Gly Val Gly Asn Ala Ser Gly Asp Trp His Cys Asp Ser Thr Trp
            20                  25                  30

Met Gly Asp Arg Val Val Thr Lys Ser Thr Arg Thr Trp Val Leu Pro
        35                  40                  45

Ser Tyr Asn Asn His Gln Tyr Arg Glu Ile Lys Ser Gly Ser Val Asp
    50                  55                  60

Gly Ser Asn Ala Asn Ala Tyr Phe Gly Tyr Ser Thr Pro Trp Gly Tyr
65                  70                  75                  80

Phe Asp Phe Asn Arg Phe His Ser His Trp Ser Pro Arg Asp Trp Gln
                85                  90                  95

Arg Leu Ile Asn Asn Tyr Trp Gly Phe Arg Pro Arg Ser Leu Arg Val
            100                 105                 110

Lys Ile Phe Asn Ile Gln Val Lys Glu Val Thr Val Gln Asp Ser Thr
        115                 120                 125

Thr Thr Ile Ala Asn Asn Leu Thr Ser Thr Val Gln Val Phe Thr Asp
    130                 135                 140

Asp Asp Tyr Gln Leu Pro Tyr Val Val Gly Asn Gly Thr Glu Gly Cys
145                 150                 155                 160

Leu Pro Ala Phe Pro Pro Gln Val Phe Thr Leu Pro Gln Tyr Gly Tyr
                165                 170                 175

Ala Thr Leu Asn Arg Asp Asn Thr Glu Asn Pro Thr Glu Arg Ser Ser
            180                 185                 190

Phe Phe Cys Leu Glu Tyr Phe Pro Ser Lys Met Leu Arg Thr Gly Asn
        195                 200                 205

Asn Phe Glu Phe Thr Tyr Asn Phe Glu Glu Val Pro Phe His Ser Ser
    210                 215                 220

Phe Ala Pro Ser Gln Asn Leu Phe Lys Leu Ala Asn Pro Leu Val Asp
225                 230                 235                 240

Gln Tyr Leu Tyr Arg Phe Val Ser Thr Asn Asn Thr Gly Gly Val Gln
                245                 250                 255

Phe Asn Lys Asn Leu Ala Gly Arg Tyr Ala Asn Thr Tyr Lys Asn Trp
            260                 265                 270

Phe Pro Gly Pro Met Gly Arg Thr Gln Gly Trp Asn Leu Gly Ser Gly
        275                 280                 285

Val Asn Arg Ala Ser Val Ser Ala Phe Ala Thr Thr Asn Arg Met Glu
    290                 295                 300

Leu Glu Gly Ala Ser Tyr Gln Val Pro Pro Gln Pro Asn Gly Met Thr
305                 310                 315                 320

Asn Asn Leu Gln Gly Ser Asn Thr Tyr Ala Leu Glu Asn Thr Met Ile
                325                 330                 335

Phe Asn Ser Gln Pro Ala Asn Pro Gly Thr Thr Ala Thr Tyr Leu Glu
            340                 345                 350

Gly Asn Met Leu Ile Thr Ser Glu Ser Glu Thr Gln Pro Val Asn Arg
        355                 360                 365
```

-continued

```
Val Ala Tyr Asn Val Gly Gly Gln Met Ala Thr Asn Asn Gln Ser Ser
    370                 375                 380

Thr Thr Ala Pro Ala Thr Gly Thr Tyr Asn Leu Gln Glu Ile Val Pro
385                 390                 395                 400

Gly Ser Val Trp Met Glu Arg Asp Val Tyr Leu Gln Gly Pro Ile Trp
                405                 410                 415

Ala Lys Ile Pro Glu Thr Gly Ala His Phe His Pro Ser Pro Ala Met
            420                 425                 430

Gly Gly Phe Gly Leu Lys His Pro Pro Pro Met Met Leu Ile Lys Asn
        435                 440                 445

Thr Pro Val Pro Gly Asn Ile Thr Ser Phe Ser Asp Val Pro Val Ser
    450                 455                 460

Ser Phe Ile Thr Gln Tyr Ser Thr Gly Gln Val Thr Val Glu Met Glu
465                 470                 475                 480

Trp Glu Leu Lys Lys Glu Asn Ser Lys Arg Trp Asn Pro Glu Ile Gln
                485                 490                 495

Tyr Thr Asn Asn Tyr Asn Asp Pro Gln Phe Val Asp Phe Ala Pro Asp
            500                 505                 510

Ser Thr Gly Glu Tyr Arg Ser Thr Arg Pro Ile Gly Thr Arg Tyr Leu
        515                 520                 525

Thr Arg Pro Leu
    530
```